(12) United States Patent
Huss et al.

(10) Patent No.: US 7,998,472 B2
(45) Date of Patent: Aug. 16, 2011

(54) CD34 STEM CELL-RELATED METHODS AND COMPOSITIONS

(75) Inventors: Ralf Huss, Waakirchen (DE); Matthias C Raggi, München (DE); Manfred J Stangl, Sauerlach (DE); Peter C Nelson, Munich (DE)

(73) Assignee: Apceth GmbH & Co. KG, München (DE)

( * ) Notice: Subject to any disclaimer, the term of this patent is extended or adjusted under 35 U.S.C. 154(b) by 0 days.

(21) Appl. No.: 12/154,059

(22) Filed: May 20, 2008

(65) Prior Publication Data

US 2009/0041735 A1    Feb. 12, 2009

Related U.S. Application Data

(60) Provisional application No. 60/931,622, filed on May 24, 2007, provisional application No. 61/003,050, filed on Nov. 14, 2007.

(51) Int. Cl.
*A61K 48/00* (2006.01)
*C12N 15/85* (2006.01)
(52) U.S. Cl. ........... 424/93.2; 514/44 A; 435/6; 435/325
(58) Field of Classification Search ........................ None
See application file for complete search history.

(56) References Cited

U.S. PATENT DOCUMENTS

| | | | | |
|---|---|---|---|---|
| 6,361,997 | B1 * | 3/2002 | Huss ............................. | 435/372 |
| 2002/0127715 | A1 * | 9/2002 | Benvenisty et al. .......... | 435/366 |
| 2003/0082155 | A1 | 5/2003 | Habener et al. | |
| 2004/0220384 | A1 * | 11/2004 | Hinuma et al. ............... | 530/350 |
| 2008/0241115 | A1 * | 10/2008 | Suh et al. .................... | 424/93.21 |

FOREIGN PATENT DOCUMENTS

| WO | WO99/37332 | 7/1999 |
|---|---|---|
| WO | WO03/010305 | 2/2003 |
| WO | WO 03/025167 | 3/2003 |
| WO | WO2004/007697 | 1/2004 |
| WO | WO2005/026335 | 3/2005 |
| WO | WO2005/093044 | 10/2005 |

OTHER PUBLICATIONS

Khalil, et al., Nonmyeloablative Stem Cell Therapy Enhances Microcirculation and Tissue Regeneration in Murine Inflammatory Bowel Disease, *Gastroenterology*, Mar. 2007 132:944-954.
Torrente, et al., Identification of a putative pathway for the muscle homing of stem cells in a muscular dystrophy model, J. Cell. Bio., vol. 162, No. 3 pp. 511-520 (2003).
Conrad et al., Adult Stem Cell Lines I Regenerative Medicine and Reconstructive Surgery, *J. Surg. Res.*, vol. 124 No. 2, pp. 201-208 (2005).
Anderson et al., The Mouse Dystrophin Muscle Promoter/Enhancer Drives Expression of Mini-dystrophin in Transgenic *mdx* Mice and Rescues the Dystrophy in These Mice, *Mol. Ther.*, Nov. 2006 vol. 14, No. 5 pp. 724-734.
Cooper et al., In vivo satellite cell activation via Myf5 and MyoD in regeneration mouse skeletal muscle, *J. Cell. Sci.*, 1999, vol. 112, No. 17 pp. 2895-2901.
Fessele S, Maier H, Zischek C, Nelson PJ, Werner T. Regulatory context is a crucial part of gene function. Trends Genet. Feb. 2002;18(2):60-3. PubMed PMID: 11818130.
Rols, et al. "Electopermeabilization of mammalian cells" Biophys J. Biophysical Society; vol. 58;pp. 1089-1098; Nov. 1990.
Schlaeger et al. Uniform vascular-endothelial-cell-specific gene expression in both embryonic and adult transgenic mice: The National Academy of Sciences of the USA; vol. 94; pp. 3058-3063, Apr. 1997.
Torchilin "Recent Approaches to Intracellular Delivery of Drugs and DNA and Organelle Targeting" Annu. Rev. Biomed. Eng. 2006. 8:343-75.
Lüttichau, et al. "Human Adult CD34_Progenitor Cells Functionally Express the Chemokine Receptors CCR1, CCR4, CCR7, CXCR5, and CCR10 but Not CXCR4" Stem Cells and Development 14:329-336 (2005).
Wennersten, et al. "Proliferation, migration, and differentiation of human neural stem/progenitor cells after transplantation into a rat model of traumatic brain injury" J Neurosurg 100:88-96, 2004.
Wu, et al. "Production of viral vectors for gene therapy applications" Department of Chemical Engineering and Center for Biotechnology and Bioengineering, 2000, 11:205-208.
Kanerva, et al. "Adenoviruses for treatment of cancer" Annals of Medicine, 2005; 37: 33-43.
Kojaoghlanian, et al. "The impact of adenovirus infection on the immunocompromised host" Rev. Med. Virol. 2003; 13: 155-171.
Lakso, et al. "Targeted oncogene activation by site-specific recombination in transgenic mice" Proc. Nail. Acad. Sci. USA vol. 89, pp. 6232-6236, Jul. 1992.
Orban, et al. "Tissue- and site-specific DNA recombination in transgenic mice" Proc. Natl. Acad. Sci. USA vol. 89, pp. 6861-6865, Aug. 1992.
Aiuti et al., Correction of ADA-SCID by Stem Cell Gene Therapy Combined with Nonmyelablative Conditioning, *Science*, New Series, vol. 296, No. 5577 (Jun. 28, 2002), pp. 2410-2413, American Association for the Advancement of Science.
Armentano, et al., Characterization of an Adenovirus Gene Transfer Vector Containing an AE4 Deletion, Human Gene Therapy 6:1343-1353 (Oct. 1995).
Atchison, et al., Adenovirus-Associated Defective Virus Particles, *Science*, New Series, vol. 149, No. 3685 (Aug. 13, 1965), pp. 754-756, American Association for the Advancement of Science.
Becerra, et al., Synthesis of Adeno-Associated Virus Structural Proteins Requires Both Alternative mRNA Splicing and Alternative Initiations from a Single Transcript, Journal of Virology, Aug. 1988, p. 2745-2754.
Gerd Bendas, Immunoliposomes a Promising Approach to Targeting Cancer Therapy, BioDrugs 2001; 15(4); 215-224.
Benihoud et al., Adenovirus vectors for gene delivery, Current Opinion in Biotechnology 1999, 10:440-447.
Bett et al., An efficient and flexible system for construction of adenovirus vectors with insertions or deletions in early regions 1 and 3, *Proc. Natl Acad. Sci. USA*, vol. 91, pp. 8802-8806 Sep. 1994.

(Continued)

Primary Examiner — Doug Schultz
(74) Attorney, Agent, or Firm — Cohen Pontani Lieberman & Pavane LLP

(57) ABSTRACT

This invention provides novel stem cell-based methods for treating a number of conditions. These methods employ CD34⁻ stem cells, and have a tremendous advantage in that they do not require myeloablation in the subject being treated. The CD34⁻ stem cells used in the instant methods can be genetically modified or not, depending on the disorder treated.

7 Claims, 11 Drawing Sheets

OTHER PUBLICATIONS

Beyer, et al., Oncoretrovirus and Lentivirus Vectors Pseudotyped with Lymphocytic Chriomeningitis Virus Glycoprotein: Generation, Concentration, and Broad Host Range, Journal of Virology, Feb. 2002, p. 1488-1495.

Bradfute et al., Adenoviral Transduction of Mouse Hemotapoietic Stem Cells, Molecular Therapy vol. 7, No. 3, Mar. 2003.

Yazawa, et al. "Current Progress in Suicide Gene Therapy for Cancer" World J. Surg. 26, 783-789, 2002 DOI: 10.1007/s00268-002-4053-5.

Young, et al. "Viral gene therapy strategies: from basic science to clinical application" Journal of Pathology J Pathol 2006; 208: 299-318.

Flierl, et al. "Adeno-associated virus-mediated gene transfer of the heart/muscle adenine nucleotide translocator (ANT) in mouse" Gene Therapy (2005) 12, 570-578.

Gabriel, et al. "Direct Observation in the Millisecond Time Range of Fluorescent Molecule Asymmetrical Interaction with the Electropermeabilized Cell Membrane" Biophysical Journal vol. 73 Nov. 1997 2630-2637.

Gaspar, et al. "Gene therapy of X-linked severe combined immunodeficiency by use of a pseudotyped gammaretroviral vector" www.thelancet.com vol. 364 Dec. 18-25, 2004.

Grill, et al. "Robust Growth of Chronically Injured Spinal Cord Axons Induced by Grafts of Genetically Modified NGF-Secreting Cells" Experimental Neurology 148, 444-452 (1997).

Hagan, et al. "Neuroprotection by human neural progenitor cells after experimental contusion in rats" M. Hagan et al. / Neuroscience Letters 351 (2003) 149-152.

Hämmerling, et al. "Vascular Integration of Endothelial Progenitors During MultistepTumor Progression" [Cell Cycle 5:5, 509-511, Mar. 1, 2006]; © 2006 Landes Bioscience.

IzsvaÂk, et al. "Sleeping Beauty, a Wide Host-range Transposon Vector for Genetic Transformation in Vertebrates" http://www.idealibrary.com on J. Mol. Biol. (2000) 302, 93-102 0022-2836.

Cavazzana-Calvo, et al., Gene Therapy of Human Severe Combined Immunodeficiency (SCID)-X1 Disease, Science, New Series, vol. 288, No. 5466 (Apr. 28, 2000), pp. 669-672, American Association for the Advancement of Science.

Cochrane, et al., Specific interaction of the human immunodeficiency virus Rev protein with a structured region in the env mRNA, Pro. Natl. Acad. Sci. USA, vol. 87, pp. 1198-1202, Feb. 1990.

Dancer, et al., Expression of thymidine kinase driven by an endothelial-specific promoter inhibits tumor growth of Lewis lung carcinoma cells in transgenic mice, Gene Therapy (2003) 10, 1170-1178.

Danthinne, et al., Production of first generation adenovirus vectors: a review, Gene Therapy (2000) 7, 1707-1714.

Danthinne, et al., New Tools for the generation of E1- and/or E3-substituted adenoviral vectors, Gene Therapy (2000) 7, 80-87.

Derossi, et al., Cell Internalization of the Third Helix of the Antennapedia Homeodomain Is Receptor-independent, The Journal of Biological Chemistry, vol. 271, No. 30, Issue of Jul. 26, pp. 18188-18193, 1996.

Dupré, et al., Efficacy of Gene Therapy for Wiskott-Aldrich Syndrome Using a WAS Promoter/cDNA-Containing Lentiviral Vector and Nonlethal Irradiation, Human Gene Therapy 17:303-313 (Mar. 2006).

Susan M. Dymecki, Flip recombinase promotes site-specific DNA recombination in embryonic stem cells and transgenic mice, Pro. Natl. Acad. Sci. USA, vol. 93, pp. 6191-6196, Jun. 1996.

Emerman, et al., Quantitative Analysis of Gene Suppression in Integrated Retrovirus Vectors, Molecular and Cellular Biology, Mar. 1986, p. 792-800.

Felnerova et al., Liposomes and virosomes as delivery systems for antigens, nucleic acid and drugs, Current Opinion in Biotechnology 2004, 15:518-529.

Aboody, et al., Stem and progenitor cell-mediated tumor selective gene therapy, Gene Therapy (2008) 15, 739-752.

Bexell, Bone Marrow Multipotent Mesenchymal Stroma Cells Act as Pericyte-like Migratory Vehicles in Experimental Gliomas, Molecular Therapy vol. 17 No. 1, 183-190 Jan. 2009.

Kucerova et al., Cytosine deaminase expressing human mesenchymal stem cells mediated tumour regression in melanoma bearing mice, The Journal of Gene Medicine 2008; 10:1071-1082.

Li, et al., Genetically engineered neural stem cells migrate and suppress glioma cell growth at distant intracranial sites, Science Direct, Cancer Letters, 251 (2007) 220-227.

Miletic, et al., Bystander Killing of Malignant Glioma by Bone Marrow-derived Tumor-Infiltrating Progenitor Cells Expressing a Suicide Gene, Molecular Therapy vol. 15 No. 7, 1373-1381 Jul. 2007.

Miyake, et al., HIV vector-mediated targeted suicide gene therapy for adult T-cell leukemia, Gene Therapy (2007), 14, 1662-1667.

Nasu, et al., Suicide Gene Therapy With Adenoviral Delivery of HSV-tk Gene for Patients With Local Recurrence of Prostate Cancer After Hormonal Therapy, The American Society of Gene Therapy, vol. 15 No. 4, 834-840 Apr. 2007.

Natsume, et al., Gene therapy for high-grade glioma, Cell Adhesion & Migration 2:3, 186-191, Jul./Aug./Sep. 2008.

Park, et al., Combination gene therapy using multidrug resistance (MDR1) gene shRNA and herpes simplex virus-thymidine kinase, Cancer Letters 261 (2008) 205-214.

Uchibori, et al., Retroviral vector-producing mesenchymal stem cells for targeted suicide cancer gene therapy, The Journal of Gene Medicine 2009; 11: 373-381.

Xu, et al., Adenoviral—mediated interleukin-18 expression in mesenchymal stem cells effectively suppresses the growth of glioma in rats, Cell Biology International 33 (2009) 466-474.

Zischek, et al., Targeting Tumor Stroma Using Engineered Mesenchymal Stem Cells Reduces the Growth of Pancreatic Carcinoma, Annals of Surgery, vol. 250, No. 5, Nov. 2009.

International Search Report, PCT/IL03/00587, Dec. 11, 2003.
European Search Report, 10163663.7, Aug. 8, 2010.
European Search Report, 10163667.8, Jul. 30, 2010.
International Search Report, PCT/US99/00395, May 13, 1999.
International Search Report, PCT/EP2010/054844, Jul. 19, 2010.
International Search Report, PCT/IL2004/000790, Apr. 5, 2005.
European Search Report, 08754569.0, Aug. 23, 2010.
International Search Report, PCT/CA02/01435, Sep. 23, 2003.

Chang, et al., "The Growth of Brain Tumors Can Be Suppressed by Multiple Transplantation of Mesenchymal Stem Cells Expressing Cytosine Deaminase", International Journal of Cancer 127, 1975-83 (2010).

Chen, et al., "Prophylaxis against carcinogenesis in three kinds of unestablished tumor models via IL12-gene-engineered MSCs", Carcinogenesis, vol. 27, No. 12, pp. 2434-2441, (2006).

Del Bo, et al., "VEGF gene variability and type 1 diabetes: evidence for a protective role", Immunogenetics, vol. 58, pp. 107-112, (2006).

Eming, et al., "Gene therapy and wound healing", Clinics in Dermatology, vol. 25, pp. 79-92, (2007).

Fathke, et al., "Contribution of Bone-Marrow-Derived Cells to Skin: Collagen Deposition and Wound Repair", Stem Cells, vol. 22, pp. 812-822, (2004).

Galmiche, et al., "Stromal cells from human long-term marrow cultures are mesenchymal cells that differentiate following a vascular smooth muscle differentiation pathway", Blood., vol. 82, pp. 66-76, (1993).

Garlanda, et al., "Heterogeneity of Endothelial Cells", Arteriosclerosis, Thrombosis, and Vascular Biology, vol. 17, pp. 1193-1202, (1997).

Huss, et al., "Chemokine Directed Homing of Transplanted Adult Stems Cells in Wound Healing and Tissue Regeneration" Verh. Dtsch. Ges, Path, vol. 88, 170-173, (2004).

Kato, et al., "Retroviral Transfer of Herpes Simplex Thymidine Kinase Gene into Glioma Cells Causes Targeting of Gancyclovir Cytotoxic Effect", Neurol Med Chir, vol. 34, pp. 339-334, (1994).

Karnoub, et al., "Mesenchymal Stem Cells within tumour stroma promote breast cancer metastasis", Nature, vol. 449, pp. 557-569, (2007).

Khalil, et al., "Nonmyeloablative Stem Cell Therapy Enhances Microcirculation and Tissue Regeneration in Murine Inflammatory Bowel Disease", Gastroenterology, vol. 132, pp. 944-954, (2007).

Kinnaird, et al., "Marrow-Derived Stromal Cells Express Genes Encoding a Broad Spectrum of Arteriogenic Cytokines and Promote in Vitro and in Vivo Arteriogenesis Through Paracrine Mechanisms", Circulation Research, vol. 94, pp. 678-685, (2004).

Komarova, et al., "Mesenchymal progenitor cells as cellular vehicles for delivery of oncolytic adenoviruses", Molecular Cancer Therapeutics, vol. 5(3), pp. 755-766, (2006).

Kucerova, et al., "Cytosine deaminase expressing human mesenchymal stem cells mediated tumour regression in melanoma bearing mice", The Journal of Gene Medicine, vol. 10, pp. 1071-1082, (2008).

Lange, et al., "Accelerated and Safe Expansion of Human Mesenchymal Stromal Cells in Animal Serum-free Medium for Transplantation and Regenerative Medicine", Cell. Physiol. vol. 213, pp. 18-26, (2007).

Lee, et al., "Multipotent stromal cells from human marrow home to and promote repair of pancreatic islets and renal glomeruli in diabetic NOD/scid mice", PNAS, vol. 103, No. 46, pp. 17438-17443, (2006).

Li, et al., "In Vitro Effect of Adenovirus-Mediated Human Gamma Interferon Gene Transfer into Human Mesenchymal Stem Cells for Chronic Myelogenous Leukemia", Hematological Oncology, vol. 24, pp. 151-158, (2006).

Li, et al., "Generation of Insulin-Producing Cells From PDX-1 Gene-Modified Human Mesenchymal Stem Cells", Cell. Physiol., vol. 211, pp. 36-44, (2007).

Loebinger, et al., "Stem cells as vectors for antitumour therapy", Thorax, vol. 65, pp. 362-369, (2010).

Miletic, et al., "Bystander Killing of Malignant Glioma by Bone Marrow-derived Tumor-Infiltrating Progenitor Cells Expressing a Suicide Gene" Molecular Therapy, vol. 15, No. 7, pp. 1373-1381, (2007).

Lu, et al., "Human Bone Marrow Mesenchymal Stem Cells Transferred with Human Insulin Genes Can Secrete Insulin Stably", Annals of Cliniacl & Laboratory Science, vol. 36, No. 2, pp. 127-136, (2006).

Moelling, et al., "Anti-tumor activity of mesenchymal stem cells producing IL-12 in a mouse melanoma model", Experimental Dermatology, vol. 15, pp. 865-874, (2006).

Moore, "Putting the neo into neoangiogenesis", The Journal of Clinical Investigation, vol. 109, pp. 313-315, (2002).

Akira Nakamizo, et al., Cancer Res. 2005:65(8):3307-3318, Apr. 15, 2005, "Human Bone Marrow-Derived Mesenchymal Stem Cells in the Treatment of Gliomas."

K. Nakamura, et al., Gene Therapy (2004) 11, 1155-1164, "Antitumor effect of genetically engineered mesenchymal stem cells in a rat glioma model."

Joachim Oswald, et al., Stem Cells 2004;22:377-384, "Mesenchymal Stem Cells Can Be Differentiated Into Endothelial Cells In Vitro."

M. Pizzato, et al., Gene Therapy (1998) 5, 1003-1007 "Production and characterization of a bicistronic Moloney-based retroviral vector expressing human interleukin 2 and herpes simplex virus thymidine kinase for gene therapy of cancer."

Susanna Purhonen, et al., "Bone marrow-derived circulating endothelial precursors do not contribute to vascular endothelium and are not needed for tumor growth" PNAS May 6, 2008, vol. 105 No. 18, 6620-6625.

Morayma Reyes, et al., "Origin of endothelial progenitors in human postnatal bone marrow", The Journal of Clinical Investigation, Feb. 2002, vol. 109, No. 3, pp. 337-346.

Berber Roorda, et al., Critical Reviews in Oncology/Hematology 69 (2009) 187-198, "Bone marrow-derived cells and tumor growth: Contribution of bone marrow-derived cells to tumor micro-environments with special focus on mesenchymal stem cells."

Hidemitsu Sato, et al., Cancer Gene Therapy (2005) 12, 757-768, "Epidermal growth factor receptor-transfected bone marrow stromal cells exhibit enhanced migratory response and therapeutic potential against murine brain tumors."

Kirsi Saukkonen, et al., "Tissue-specific promoters for cancer gene therapy" Expert Opin. Biol. Ther. (2004) 4(5), pp. 683-696.

Thorsten M. Schlaeger, et al., Proc. Natl. Acad. Sci. USA vol. 94, pp. 3058-3063, Apr. 1997 "Uniform vascular-endothelial-cell-specific gene expression in both embryonic and adult transgenic mice."

Herbert Spring, et al., PNAS, Dec. 13, 2005, vol. 102, No. 50, 18111-116 "Chemokines direct endothelial progenitors into tumor neovessels."

John Stagg, et al., Human Gene Therapy, 15:597-608 (Jun. 2004) "Marrow Stromal Cells for Interlukin-2 Delivery in Cancer Immunotherapy."

Mariam A. Stoff-Khalili, et al., "Mesenchymal stem cells as a vehicle for targeted delivery of CRAds to lung metastases of breast carcinoma", Breast Cancer Res Treat, vol. 105, pp. 157-167, (2007).

Studeny, et al., "Mesenchymal Stem Cells: Potentional Precursors for Tumor Stroma and Targeted-Delivery Vehicles for Anticancer Agents", Journal of National Cancer Institute, vol. 96, No. 21, pp. 1593-1603, (2004).

Vilalta, et al., "Human adipose tissue-derived mesenchymal stromal cells as vehicles for tumor bystander effect: a model based on bioluminescence imaging", Gene Therapy, vol. 16, pp. 547-557, (2009).

Von Luttichau, et al., "Human Adult $CD34^-$ Progenitor Cells Functionaly Express the Chemokine Receptors CCR1, CCR4, CCR7, CXCR5, and CCR10 but not CXCR4", Stem Cells and Development, vol. 14, pp. 329-336, (2005).

Wickersheim, et al., "Endothelial progenitor cells do not contribute to tumor endothelium in primary and metastatic tumors", Int. J. Cancer, vol. 125, pp. 1771-1777 (2009).

Wu, et al., "Mesenchymal stem cells enhance wound healing through differentiation and angiogenesis", Stem Cells, vol. 25, pp. 2648-2659, (2007).

Xin, et al., "Targeted Delivery of CX3CL1 to Multiple Lung Tumors by Mesenchymal Stern Cells", Stem Cells, vol. 25, pp. 1618-1626, (2007).

Yoder, et al., "Endothelial progenitor cell: ongoing controversy for defining these cells and their role in neoangiogenesis in the murine system", Current Opinion in Hematology, vol. 16, pp. 269-273, (2009).

Zacharek, et al., "Angiopoietin/Tie2 and VEGF/Flk1 induced by MSC treatment amplifies angiogenesis and vascular stabilization after stroke", Journal of Cerebral Blood Flow & Metabolism, vol. 27, pp. 1684-1691 (2007).

Zischek, et al., "Targeting Tumor Stroma Using Engineered Mesenchymal Stem Cells Reduces the Growth of Pancreatic Carcinoma", Annals of Surgery, vol. 250, No. 5, pp. 747-753, (2009).

Hoffmann, et al. "Microcirculatory disorders in sepsis and transplantation: therapy with natural coagulatory inhibitors antithrombin and activated protein C.", U.S. National Library of Medicine National Institutes of Health; 12(5):426-30, Oct. 2006 (Abstract).

Jung, et al., "Primary and secondary mircrocirculatory disorders in essential hypertension", The Clin. Invest., 71:132-138. 1993.

Schmid, "[What is a microcirculatory disorder in chronic degenerative vascular disease? (author's transl.)]", U.S. National Library of Medicine National Institutes of Health, 31:1997-2007, 1981.

Elzaouk, et al., "Anti-tumor activity of mesenchymal stem cells producing IL-12 in a mouse melanoma model", Experimental Dermatology, 15:865-874, 2006.

* cited by examiner

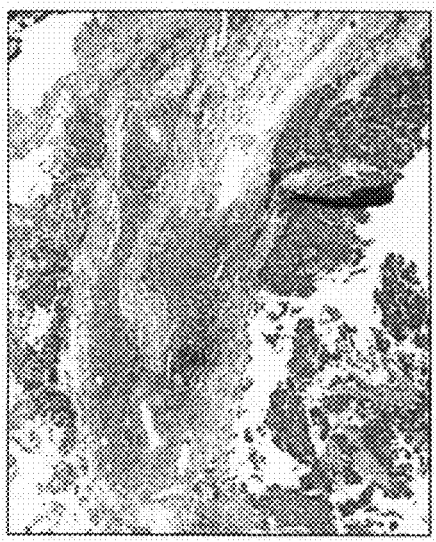
FIG. 8
BREAST TUMOR CONTROL.
NORMAL BREAST CONTROL.
CONTROL TUMOR — ADDITION OF CONTROL imMSC
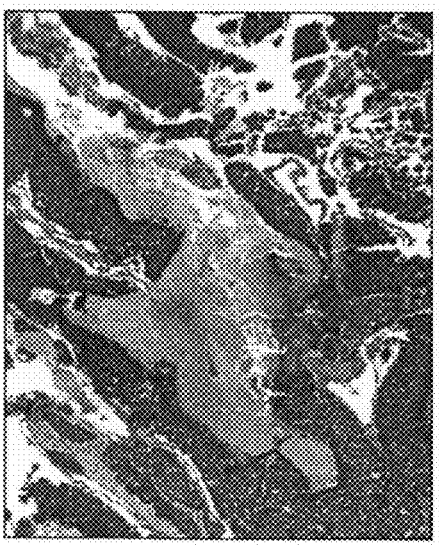
TREATED FOR FOUR WEEKS (18–22) WITH imMSC/TK + GV I.V.

CD34 STEM CELL-RELATED METHODS AND COMPOSITIONS

RELATED APPLICATIONS

This application claims priority from U.S. Provisional Patent Application Ser. No. 60/931,622 which was filed on May 24, 2007 and U.S. Provisional Patent Application Ser. No. 61/003,050 which was filed on Nov. 14, 2007.

BACKGROUND OF THE INVENTION

Field of the Invention

Throughout this application, various publications are cited. The disclosure of these publications, as well as of the above-identified provisional applications, is hereby incorporated by reference into this application to describe more fully the state of the art to which this invention pertains.

Stem cells mediate the reproduction and transmission of genetic information to subsequent cellular generations. They can self-renew and generate differentiated progeny. In recent years progress has been made in our understanding of the molecular mechanisms that underlie the interactions between stem cells and their tissue niches. This has led to a better understanding of the molecular regulatory mechanisms at work in stem cells.

While gene therapy is still an experimental approach, the technology holds promise for making an impact on human health. The scope and definition of gene therapy has changed and expanded over the past few years. In addition to correcting inherited genetic disorders such as cystic fibrosis, hemophilia and others entities, gene therapy approaches are also being developed to combat acquired diseases such as cancer, AIDS, chronic vascular ischemia, osteoarthritis, diabetes, Parkinson's and Alzheimer's disease.

At present, germ line gene therapy is not being contemplated due to its complex technical nature and ethical considerations. However, somatic cell gene therapy exclusively for the benefit of one individual (that cannot be passed on to succeeding generations) is a major focus of stem cell research. It has taken over 15 years of effort from the initial description of successful gene transfer into murine hematopoietic stem cells, to the first unambiguously successful clinical trials in patients born with x-linked combined immunodeficiency (SCID) and adenosine deaminase deficiency (ADA)-deficiency (Aiuti et al., 2002; Cavazzana-Calvo et al., 2000; Gaspar et al., 2004). Many aspects of stem cell therapy are being explored. For example, retroviral vectors have been used in many settings for the transfer of genes into stem cells to repair mutated or incomplete genes. These include severe combined immune deficiencies, Fanconi anemia and other hemoglobinopathies (Herzog et al., 2006).

A central issue in stem cell engineering is the specific methodology used to introduce therapeutic genes into the progenitor cells. Because retroviruses tend to insert into active genes (it is thought that condensed chromatin opens up in these regions), it has been suggested that their use may also increase the risk of cancer (Young et al., 2006), because the insertion of retroviral vectors proximal to genes involved in cell proliferation could in theory generate a precursor cancer stem cell. However, the overall risk of this type of event is difficult to establish. There are now many examples of complete success achieved in patients with chronic granulomatous disease (CGD) where NADPH oxidase activity was restored following the infusion of genetically altered blood stem cells (Barese et al., 2004).

The minimal requirement for productive gene therapy is the sustained production of the therapeutic gene product in the correct biological context with minimal harmful side effects. To achieve this end, the application of stem cells in genetic therapy will require the development of new strategies for modulating therapeutic gene expression, as well as methods for the efficient delivery of foreign genes into stem cells. The selective control of therapeutic gene expression by differentiating stem cells within a defined tissue environment is an important goal in stem cell engineering. This approach could, for example, help in the control of stem cell differentiation into specific lineages, the maintenance of their undifferentiated state for later transplantation, proliferation, and the regulation of expression of therapeutic genes such as suicide genes, cytokines or growth factors in defined tissue environments.

SUMMARY OF THE INVENTION

This invention provides a method for treating a subject afflicted with a gastrointestinal disorder comprising introducing into the subject's bloodstream a therapeutically effective number of $CD34^-$ stem cells, wherein (a) the $CD34^-$ stem cells are not genetically modified, (b) the introduction of the $CD34^-$ stem cells is not preceded, accompanied or followed by myeloablation, and (c) the gastrointestinal disorder is characterized by a need for cell proliferation in the gastrointestinal endothelium.

This invention also provides a method for treating a diabetic subject or a pre-diabetic subject comprising introducing into the subject's bloodstream a therapeutically effective number of $CD34^-$ stem cells, wherein (a) the $CD34^-$ stem cells are not genetically modified, and (b) the introduction of the $CD34^-$ stem cells is not preceded, accompanied or followed by myeloablation.

This invention further provides a method for treating a subject afflicted with muscular dystrophy comprising introducing into the subject's bloodstream a therapeutically effective number of non-autologous $CD34^-$ stem cells, wherein (a) the $CD34^-$ stem cells are not genetically modified, and (b) the introduction of the $CD34^-$ stem cells is not preceded, accompanied or followed by myeloablation.

This invention further provides a method for improving microcirculation and/or acute wound healing in a subject who is about to undergo, is undergoing or has undergone surgery comprising introducing into the subject's bloodstream a therapeutically effective number of $CD34^-$ stem cells, wherein (a) the $CD34^-$ stem cells are introduced into the subject's bloodstream immediately prior to, during, and/or immediately following surgery, (b) the $CD34^-$ stem cells are not genetically modified, and (c) the introduction of the $CD34^-$ stem cells is not preceded, accompanied or followed by myeloablation.

This invention further provides a method for improving microcirculation and/or acute wound healing in a subject who is about to undergo, is undergoing or has undergone a physical trauma comprising introducing into the subject's bloodstream a therapeutically effective number of $CD34^-$ stem cells, wherein (a) the $CD34^-$ stem cells are introduced into the subject's bloodstream immediately prior to, during, and/or immediately following the physical trauma, (b) the $CD34^-$ stem cells are not genetically modified, and (c) the introduction of the $CD34^-$ stem cells is not preceded, accompanied or followed by myeloablation.

This invention provides a method for treating a subject afflicted with a tumor comprising introducing into the subject's bloodstream a therapeutically effective number of genetically modified CD34⁻ stem cells, wherein (a) each of the genetically modified CD34⁻ stem cells contains an exogenous nucleic acid comprising (i) a cytotoxic protein-encoding region operably linked to (ii) a promoter or promoter/enhancer combination, whereby the cytotoxic protein is selectively expressed when the genetically modified CD34⁻ stem cells come into proximity with, and differentiate in proximity with, tumor tissue undergoing angiogenesis, and (b) the introduction of the genetically modified CD34⁻ stem cells is not preceded, accompanied or followed by myeloablation.

This invention further provides a method for treating a subject afflicted with a gastrointestinal disorder comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which enhances endothelial cell growth, which region is operably linked to (ii) an endothelium-specific promoter or promoter/enhancer combination, (b) the introduction of the genetically modified CD34⁻ stem cells is not preceded, accompanied or followed by myeloablation, and (c) the gastrointestinal disorder is characterized by a need for cell proliferation in the gastrointestinal endothelium.

This invention further provides a method for treating a diabetic subject or a pre-diabetic subject comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which enhances endothelial cell growth, which region is operably linked to (ii) an endothelium-specific promoter or promoter/enhancer combination, and (b) the introduction of the genetically modified CD34⁻ stem cells is not preceded, accompanied or followed by myeloablation.

This invention further provides a method for treating a subject afflicted with muscular dystrophy comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which is absent from or underexpressed in the subject's muscle cells or whose overexpression in the subject's muscle cells is desired, which region is operably linked to (ii) a muscle-specific promoter or muscle-specific promoter/enhancer combination, and (b) the introduction of the genetically modified CD34⁻ stem cells is not preceded, accompanied or followed by myeloablation.

This invention further provides a method for improving microcirculation and/or acute wound healing in a subject who is about to undergo, is undergoing or has undergone surgery comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which enhances endothelial cell growth, which region is operably linked to (ii) an endothelium-specific promoter or promoter/enhancer combination, and (b) the introduction of the genetically modified CD34⁻ stem cells is not preceded, accompanied or followed by myeloablation.

Finally, this invention provides a method for improving microcirculation and/or acute wound healing in a subject who is about to undergo, is undergoing or has undergone a physical trauma comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which enhances endothelial cell growth, which region is operably linked to (ii) an endothelium-specific promoter or promoter/enhancer combination, and (b) the introduction of the genetically modified CD34⁻ stem cells is not preceded, accompanied or followed by myeloablation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

Figure 1:
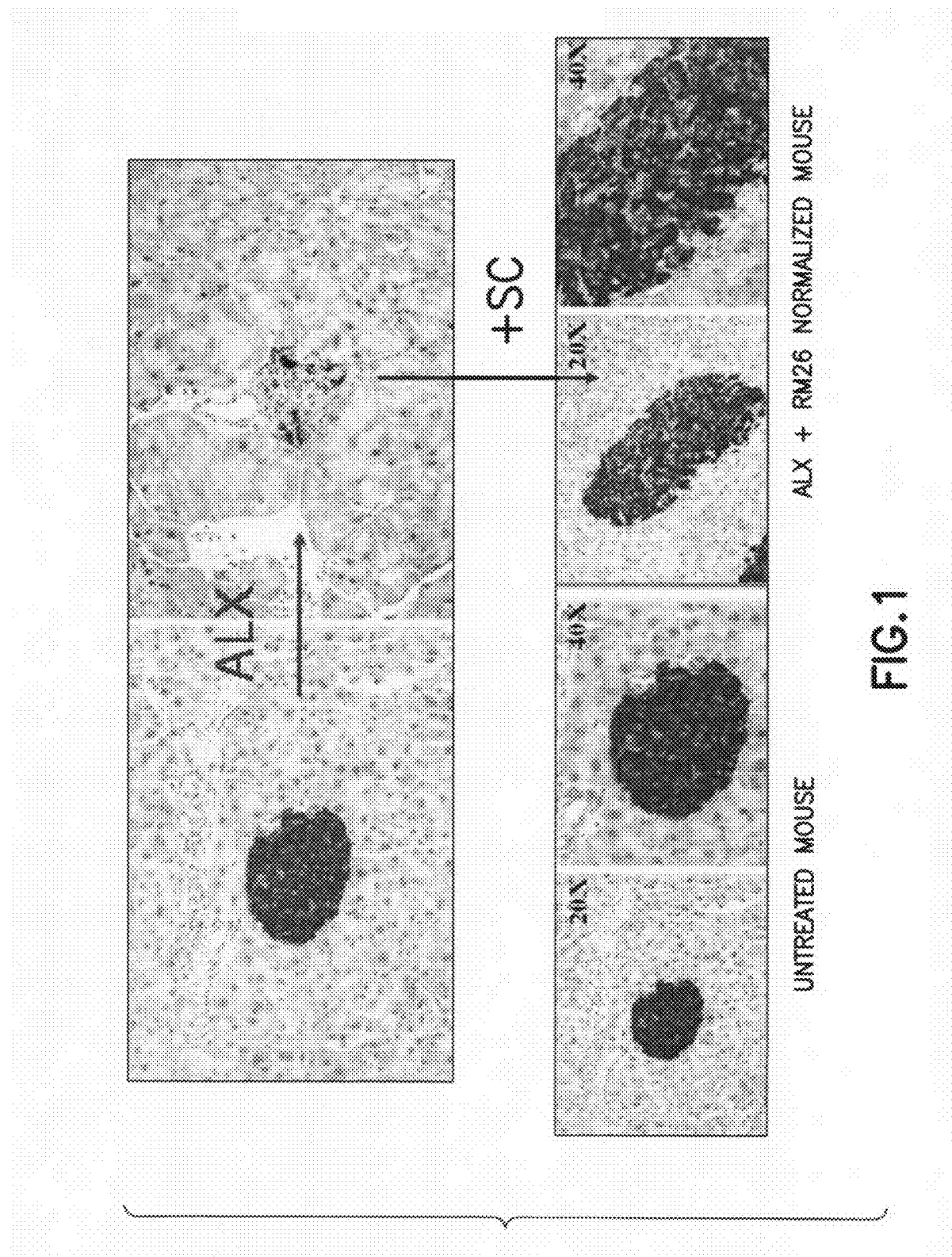
FIG. 1
Figure 2:
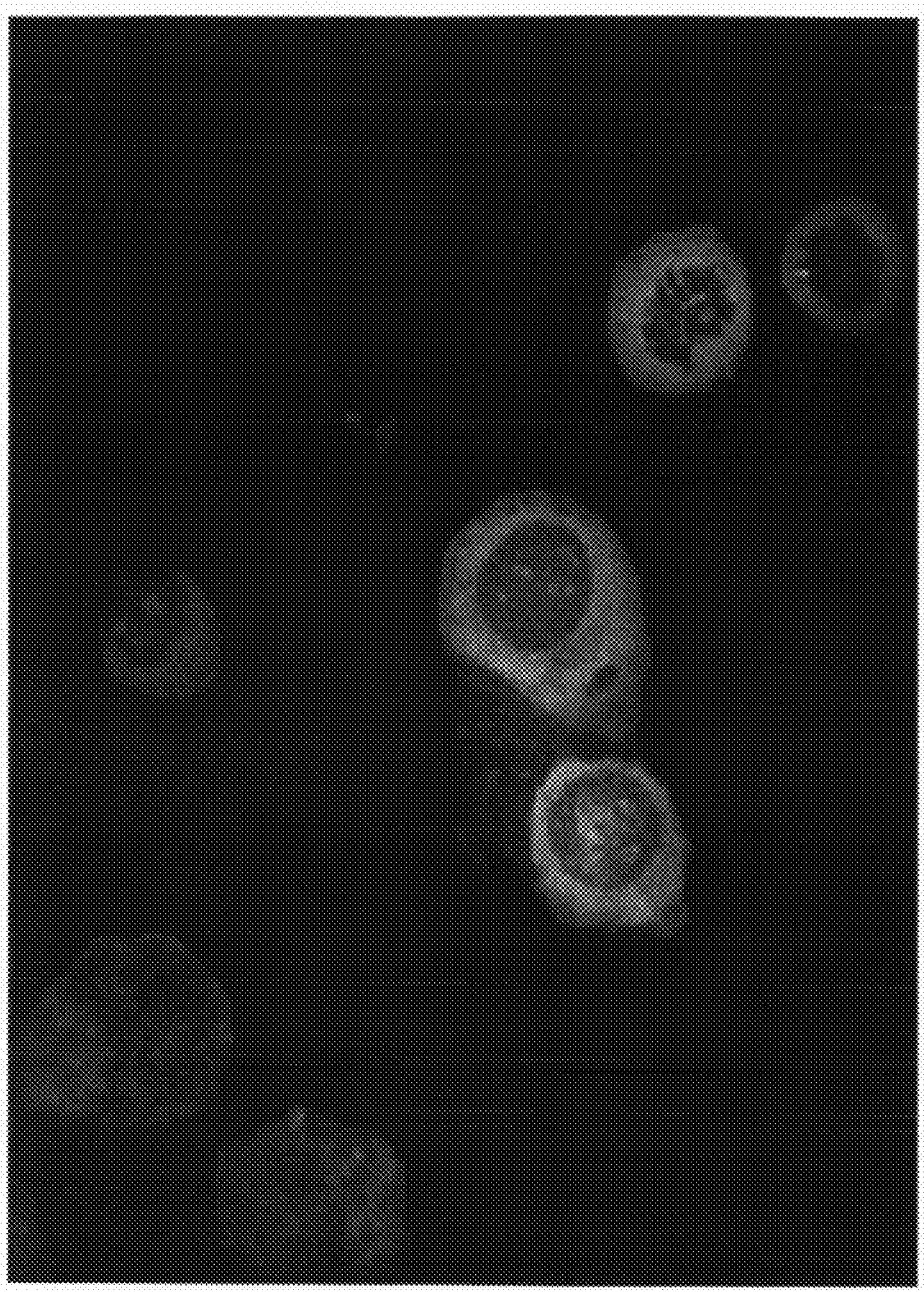
Figure 3:
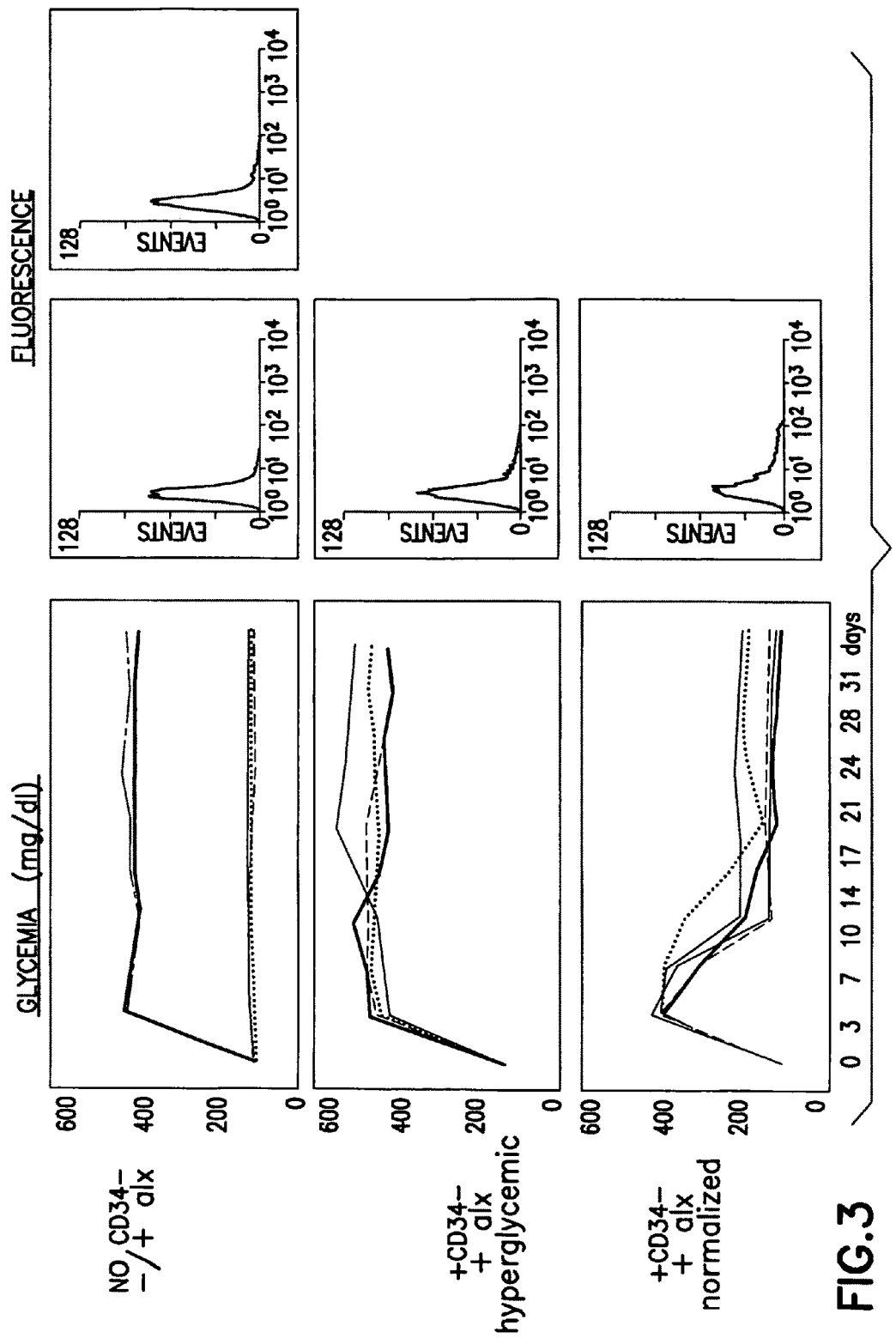
Figure 4:
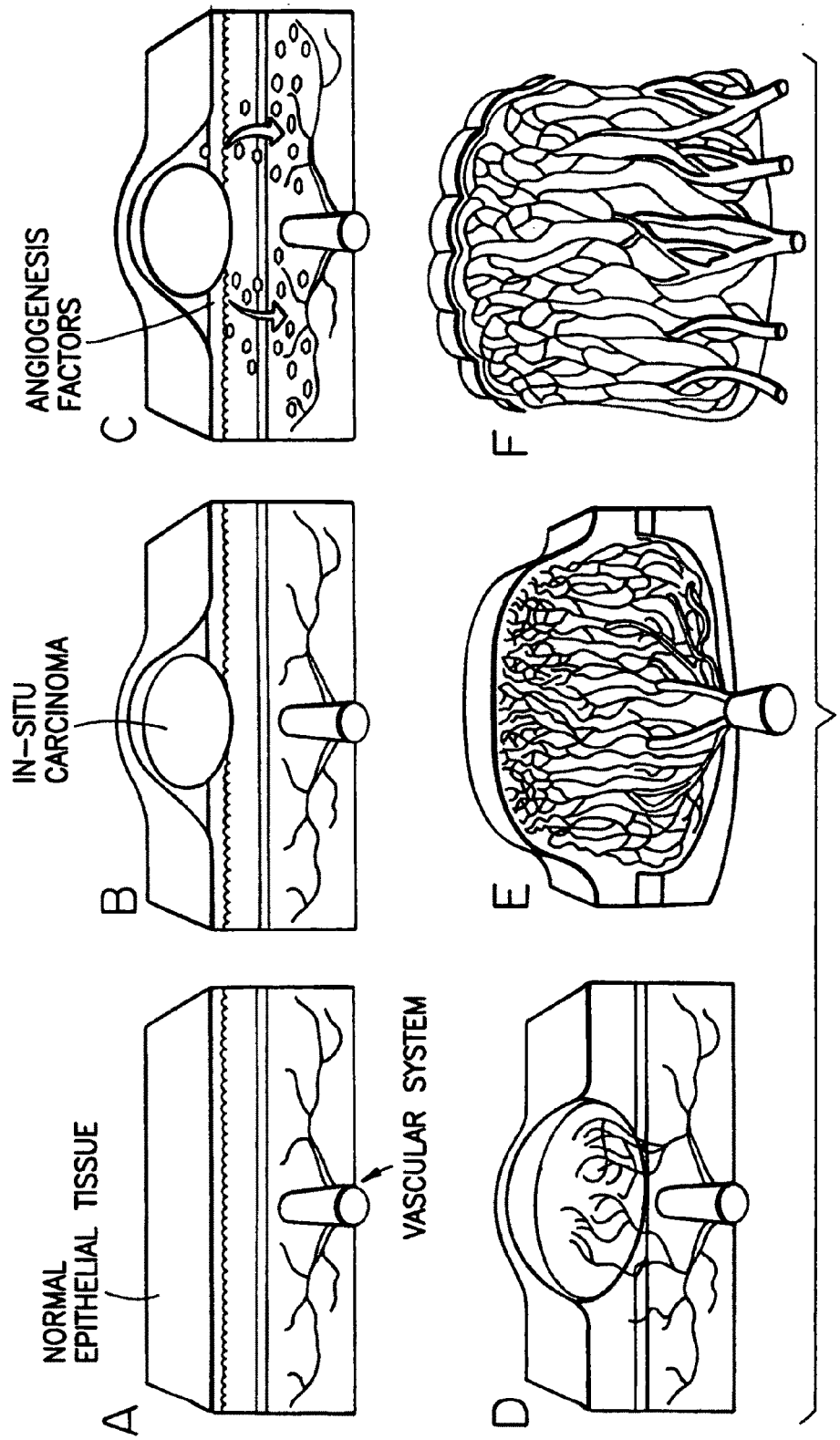

Top row: expression of insulin in a normal murine β-islet before (left) and after alloxan (ALX) treatment (right) with almost complete insulin depletion. Bottom row: size of a normal insulin producing β-islet at different magnification (20×; 40×); the treatment of insulin-depleted β-islet after ALX treatment with CD34-negative stem cells (SC) completely restores insulin production with signs of hypertrophy (20× and 40×).

FIG. 2

Isolated cells from a murine pancreas after ALX-induced diabetes and SC restoration of insulin production. The transplanted CD34-negative stem cells were marked with a constitutively expressed green fluorescence protein, and the insulin-producing cells showed a red fluorescence. There was no co-expression of both markers, suggesting that the transplanted stem cells do not express insulin by themselves but rather facilitate the endogenous regeneration.

FIG. 3

Left: Blood glucose levels of mice after ALX treatment without SC transplantation (top), with SC transplantation and no correction of the blood glucose level (middle) and mice with a normalized blood glucose level after SC transplantation (bottom). Right: Only mice that revealed the presence of stem cells in their pancreas (homogenized for FACS analysis and detection of green fluorescence) (E3; circle) showed a normalized blood glucose level, suggesting the pivotal role of transplanted cells in the correction of insulin production.

FIG. 4

Schematic presentation of the development of an epithelial malignancy from an in-situ carcinoma to invasive cancer and the connection to the endogenous blood vessel system. CD34-negative stem cells home to a site of neo-angiogenesis as demonstrated here and can therefore be utilized as a Trojan Horse to deliver cytotoxic or immune modulatory agents.

FIG. 5

Detection RFP-positive cells in mammary tumors. Tie2-RFP transfected stem cells differentiate to endothelial and transcribe the RFP. (A) Counterstained with DAPI. (B) RFP-positive cells forming vessels.

FIG. 6

Reduced tumor progression under GCV treatment. (A) Stem cell-GCV application protocol. The cell suspension (day 0) and the GCV-solution (day 5-8) respectively were applied as shown. Increase of bodyweight during the treatment of mice reflected the total tumor load as all breasts were involved. Body weight was measured on day 0 and 5 of each cycle of therapy and the day of dissection. (B) Groups of mice, treatment starting in week 22, average showing standard deviation. Mice were sorted in one treatment group and two control groups. First control group received 1×PBS instead of a stem cell suspension and no drug-injection (dashed line); the second control group received a stem cell suspension transfected with Tie2-RFP but no GCV (dotted line). The treatment group received stem cells and GCV as shown in A, (solid line). (C) Groups of treatment starting in week 18, average and standard deviation.

FIG. 7

Age at dissection. Controls vs. treatment group of mice starting treatment at week 22. Note the significant difference in time to reach similar tumor sizes (see table 1) and the extended life span of mice after successful treatment with MSC TK-vehicles and GCV.

FIG. 8

Tumor regrowth model: Primary breast tumor was resected at 18 weeks and MSC/tk treatment was initiated during regrowth of the tumor.

FIG. 9

MSC—expressing green florescent protein (GFP) home to the growing pancreatic tumor. In parallel experiments, MSC engineered to express red florescent protein (RFP) under the control of the Tie2 promoter/enhancer show a directed expression in the tumor vasculature. Top row: MSC engineered to express GFP under the control of the CMV promoter home to the tumor following i.v. injection. Bottom row: MSC engineered to express RFP under the control of the Tie2.

FIG. 10

The effect of the tk/GCV treatment was then assessed after the injection of the C57Bl/6 MSC (Tie2-tk) cells.

The treatment regimen was essentially as described for the breast cancer study. 500,000 cells were injected on day one, followed by three days where the cells were allowed to be recruited to the growing tumor and to differentiate into endothelial-like Tie2 expressing cells thus expressing the TK suicide gene. The mice were then treated for four days with GVC. After one day of rest, the cycle repeated for the duration of the experiment.

FIG. 11

Figure shows an additional example of the effect of treatment of the orthotopic pancreatic tumor with therapeutic stem cells together with GCV. A dramatic reduction in tumor size (50%) as well as reduced peritoneal carcinosis was seen in comparison to the untreated group.

DETAILED DESCRIPTION OF THE PRESENTLY PREFERRED EMBODIMENTS

Terms

In this application, certain terms are used which shall have the meanings set forth as follows.

As used herein, "acute wound healing" shall include, without limitation, a cellular and molecular process which is activated to repair tissue from the moment of injury under the control of biological and mechanical signals. Successful acute wound healing occurs when a dynamic balance is met between the loads placed across a provisional matrix and the feedback of repair cells.

As used herein, a cell is "allogenic" with respect to a subject if it or any of its precursor cells are from another subject of the same species.

As used herein, a cell is "autologous" with respect to a subject if it or its precursor cells are from that same subject.

As used herein, "CD34⁻ stem cell" shall mean a stem cell lacking CD34 on its surface. CD34⁻ stem cells, and methods for isolating same, are described, for example, in Lange C. et al., Accelerated and safe expansion of human mesenchymal stromal cells in animal serum-free medium for transplantation and regenerative medicine. *J. Cell Physiol.* 2007, Apr. 25 [Epub ahead of print].

As used herein, "cell proliferation" shall mean the division, growth in size and/or differentiation of cells.

As used herein, "cytotoxic protein" shall mean a protein which, when present in, on and/or in proximity with a cell, causes that cell's death directly and/or indirectly. Cytotoxic proteins include, for example, suicide proteins (e.g. HSV-tk) and apoptosis inducers. Cytotoxic genes include null genes, siRNA or miRNA for gene knockdown (e.g. CCR5−/−). A number of suicide gene systems have been identified, including the herpes simplex virus thymidine kinase gene, the cytosine deaminase gene, the varicella-zoster virus thymidine kinase gene, the nitroreductase gene, the *Escherichia coli* gpt gene, and the *E. coli* Deo gene. Cytosine deaminase; Cytochrome P450; Purine nucleoside phosphorylase; Carboxypeptidase G2; Nitroreductase. As detailed in: Yazawa K, Fisher W E, Brunicardi F C: Current progress in suicide gene therapy for cancer. World J Surg. 2002 July; 26 (7):783-9. Cytotoxic factors include the following: (i) homing factors such as chemokines and mucin chemokine GPI fusions (chemokine derived agents can be used to facilitate the directed recruitment of engineered stem cells, see, e.g., PCT International Application No. PCT/EP2006/011508, regarding mucin fusions anchored with GPI); (ii) viral antigens (measles, chicken pox) as cytotoxic proteins; and (iii) Her2/neu antigens which can be presented on the surfaces of engineered stem cells, followed by administration of her-2/neu antibody, and CamPath® (Alemtuzumab) directed against a CD52 epitope.

As used herein, "endothelial cell" shall include, without limitation, a cell that forms the inner lining of the intima in blood vessels during or after a process called angiogenesis. The factors controlling this process are called angiogenic factors. Endothelial cells also act with circulating blood cells by means of receptor-ligand interactions.

As used herein, an "endothelium-specific promoter or promoter/enhancer combination" is a promoter or promoter/enhancer combination, respectively, which when in an endothelial cell in or in proximity with endothelial cells, causes expression of an operably linked encoding region more than it would in any other milieu in the subject.

As used herein, a nucleic acid is "exogenous" with respect to a cell if it has been artificially introduced into that cell or any of that cell's precursor cells.

As used herein, "gastrointestinal disorder" shall mean any disorder of the stomach, small intestine and/or large intestine.

As used herein, a stem cell is "genetically modified" if either it or any of its precursor cells have had nucleic acid artificially introduced thereinto. Methods for generating genetically modified stem cells include the use of viral or non-viral gene transfer (e.g., plasmid transfer, phage integrase, transposons, AdV, AAV and Lentivirus).

As used herein, "immediately prior to" an event includes, for example, within 5, 10 or 30 minutes prior to, or 1, 2, 6, 12 or 24 hours prior to the event. "Immediately following" an event includes, for example, within 5, 10 or 30 minutes after, or 1, 2, 6, 12 or 24 hours after to the event.

As used herein, "integration" of a nucleic acid into a cell can be transient or stable.

As used herein, "introducing" CD34⁻ stem cells "into the subject's bloodstream" shall include, without limitation, introducing such cells into one of the subject's veins or arteries via injection. Such administering can also be performed, for example, once, a plurality of times, and/or over one or more extended periods. A single injection is preferred, but repeated injections over time (e.g., quarterly, half-yearly or yearly) may be necessary in some instances. Such administering is also preferably performed using an admixture of CD34⁻ stem cells and a pharmaceutically acceptable carrier. Pharmaceutically acceptable carriers are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in *Remington: The Science and Practice of Pharmacy*, 20$^{th}$ Ed., p. 808, Lippincott Williams & Wilkins (2000). Preservatives and other additives may also be present, such as, for example, antimicrobials, antioxidants, chelating agents, inert gases, and the like.

As used herein, "microcirculation" shall include, without limitation, the flow of blood from aterioles to capillaries or sinusoids to venules. Under certain circumstances, the term microcirculation is also applied to lymphatic vessels.

As used herein, "myeloablation" shall mean the severe or complete depletion of bone marrow cells caused by, for example, the administration of high doses of chemotherapy or radiation therapy. Myeloablation is a standard procedure and is described, for example, in Deeg H J, Klingemann H G, Philips G L, *A Guide to Bone Marrow Transplantation*. Springer-Verlag Berlin Heidelberg 1992.

As used herein, a stem cell is "not genetically modified" if neither it nor any of its precursor cells have had nucleic acid artificially introduced thereinto.

As used herein, "nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

As used herein, a cytotoxic protein-encoding nucleic acid region is "operably linked" to a promoter or promoter/enhancer combination if such promoter or promoter/enhancer combination causes the expression of the cytotoxic protein.

As used herein, a "polypeptide" means a polymer of amino acid residues. A "peptide" typically refers to a shorter polypeptide (e.g., 10 amino acid residues), and a "protein" typically refers to a longer polypeptide (e.g., 200 amino acid residues). The amino acid residues can be naturally occurring or chemical analogues thereof. Polypeptides can also include modifications such as glycosylation, lipid attachment, sulfation, hydroxylation, and ADP-ribosylation.

As used herein, a "prediabetic" subject includes, without limitation, a subject who has the complex of symptoms that indicate he will likely develop insulin-dependent diabetes. Prediabetic subjects have a higher-than-normal insulin levels.

As used herein, a "promoter" includes, without limitation, endothelin-1 promoter, pre-proendothelin-1 promoter, myoD promoter, NeuroD promoter, CD20 promoter, insulin promoter, Pdx-1 promoter, VEGF promoter, VEGF-R promoter, SCL promoter, Sca1 promoter, BDNF(-R) promoter, NGF(-R) promoter and EGF-R promoter.

As used herein, "promoter/enhancers" include, without limitation, Tie2 promoter enhancer, and Flk1 promoter and intronic enhancer.

As used herein, in "proximity with" a tissue includes, for example, within 1 mm of the tissue, within 0.5 mm of the tissue and within 0.25 mm of the tissue.

As used herein, a cytotoxic protein is "selectively expressed" when a genetically modified CD34⁻ stem cell encoding same comes into proximity with, and differentiates in proximity with, tumor tissue undergoing angiogenesis, if the cytotoxic protein is expressed in that milieu more than it is expressed in any other milieu in the subject. Preferably, the cytotoxic protein is expressed in that milieu at least 10 times more than it is expressed in any other milieu in the subject.

As used herein, "subject" shall mean any animal, such as a human, non-human primate, mouse, rat, guinea pig or rabbit.

As used herein, a "therapeutically effective number of CD34⁻ stem cells" includes, without limitation, the following amounts and ranges of amounts: (i) from about $1 \times 10^2$ to about $1 \times 10^8$ cells/kg body weight; (ii) from about $1 \times 10^3$ to about $1 \times 10^7$ cells/kg body weight; (iii) from about $1 \times 10^4$ to about $1 \times 10^6$ cells/kg body weight; (iv) from about $1 \times 10^4$ to about $1 \times 10^5$ cells/kg body weight; (v) from about $1 \times 10^5$ to about $1 \times 10^6$ cells/kg body weight; (vi) from about $5 \times 10^4$ to about $0.5 \times 10^5$ cells/kg body weight; (vii) about $1 \times 10^3$ cells/kg body weight; (viii) about $1 \times 10^4$ cells/kg body weight; (ix) about $5 \times 10^4$ cells/kg body weight; (x) about $1 \times 10^5$ cells/kg body weight; (xi) about $5 \times 10^5$ cells/kg body weight; (xii) about $1 \times 10^6$ cells/kg body weight; and (xiii) about $1 \times 10^7$ cells/kg body weight. Human body weights envisioned include, without limitation, about 50 kg, about 60 kg; about 70 kg; about 80 kg, about 90 kg; and about 100 kg. These numbers are based on pre-clinical animal experiments and standard protocols from the transplantation of CD34+ hematopoietic stem cells. Mononuclear cells (including CD34⁺ cells) usually contain between 1:23,000 to 1:300,000 CD34⁻ cells.

As used herein, "treating" a subject afflicted with a disorder shall mean slowing, stopping or reversing the disorder's progression. In the preferred embodiment, treating a subject afflicted with a disorder means reversing the disorder's progression, ideally to the point of eliminating the disorder itself. As used herein, ameliorating a disorder and treating a disorder are equivalent.

As used herein, "tumor" shall include, without limitation, a vascularized tumor such as a prostate tumor, a pancreatic tumor, a squamous cell carcinoma, a breast tumor, a melanoma, a basal cell carcinoma, a hepatocellular carcinoma, testicular cancer, a neuroblastoma, a glioma or a malignant astrocytic tumor such as glioblastma multiforme, a colorectal tumor, an endometrial carcinoma, a lung carcinoma, an ovarian tumor, a cervical tumor, an osteosarcoma, a rhabdo/leiomyosarcoma, a synovial sarcoma, an angiosarcoma, an Ewing sarcoma/PNET and a malignant lymphoma. These include primary tumors as well as metastatic diseases.

As used herein, a cell is "xenogenic" with respect to a subject if it or any of its precursor cells are from another subject of a different species.

Embodiments of the Invention

This invention provides novel stem cell-based methods for treating certain conditions. These methods employ CD34⁻ stem cells, as opposed to later stage stem cells, and have a tremendous advantage in that they do not require myeloablation for the subject being treated. The CD34⁻ stem cells used in the instant methods can be genetically modified or not, depending on the disorder treated. The instant methods are detailed below, beginning with methods employing non-genetically modified CD34⁻ stem cells and followed by methods employing genetically modified CD34⁻ stem cells.

Specifically, this invention provides a method for treating a subject afflicted with a gastrointestinal disorder comprising introducing into the subject's bloodstream a therapeutically effective number of CD34⁻ stem cells, wherein (a) the CD34⁻ stem cells are not genetically modified, (b) the introduction of the CD34⁻ stem cells is not preceded, accompanied or followed by myeloablation, and (c) the gastrointestinal disorder is characterized by a need for cell proliferation in the gastrointestinal endothelium.

In this method, the gastrointestinal disorder includes, without limitation, colitis, ulcerative colitis, inflammatory bowel disorder, Crohn's disease, colitis due to acute and chronic intestinal ischemia, celiac disease, Whipple disease, or Graft-versus-Host disease after stem cell transplantation.

This invention also provides a method for treating a diabetic subject or a pre-diabetic subject comprising introducing into the subject's bloodstream a therapeutically effective number of CD34⁻ stem cells, wherein (a) the CD34⁻ stem cells are not genetically modified, and (b) the introduction of the CD34⁻ stem cells is not preceded, accompanied or followed by myeloablation.

In one embodiment of this method, the subject is pre-diabetic, either for type I diabetes or type II diabetes. In another embodiment, the subject is diabetic, afflicted either with type I diabetes or type II diabetes.

This invention further provides a method for treating a subject afflicted with muscular dystrophy comprising introducing into the subject's bloodstream a therapeutically effective number of non-autologous CD34⁻ stem cells, wherein (a) the CD34⁻ stem cells are not genetically modified, and (b) the introduction of the CD34⁻ stem cells is not preceded, accompanied or followed by myeloablation.

In the preferred embodiment of this method, the subject is afflicted with Duchenne or Becker's muscular dystrophy, and the CD34⁻ stem cells are allogenic with respect to the subject.

This invention further provides a method for improving microcirculation and/or acute wound healing in a subject who is about to undergo, is undergoing or has undergone surgery comprising introducing into the subject's bloodstream a therapeutically effective number of CD34⁻ stem cells, wherein (a) the CD34⁻ stem cells are introduced into the subject's bloodstream immediately prior to, during, and/or immediately following surgery, (b) the CD34⁻ stem cells are not genetically modified, and (c) the introduction of the CD34⁻ stem cells is not preceded, accompanied or followed by myeloablation.

This method is appropriate for any type of surgery including, without limitation, abdominal surgery, thoracic surgery, neurosurgery, plastic surgery or trauma surgery. Additionally, the surgery can be laproscopic surgery or open surgery.

This invention further provides a method for improving microcirculation and/or acute wound healing in a subject who is about to undergo, is undergoing or has undergone a physical trauma comprising introducing into the subject's bloodstream a therapeutically effective number of CD34⁻ stem cells, wherein (a) the CD34⁻ stem cells are introduced into the subject's bloodstream immediately prior to, during, and/or immediately following the physical trauma, (b) the CD34⁻ stem cells are not genetically modified, and (c) the introduction of the CD34⁻ stem cells is not preceded, accompanied or followed by myeloablation.

This method is appropriate for any type of physical trauma. Specifically envisioned are (i) childbirth, wherein the CD34⁻ stem cells are introduced into the subject's bloodstream immediately prior to, during or immediately following the event, (ii) a flesh wound caused by a violent act, wherein the CD34⁻ stem cells are introduced into the subject's bloodstream immediately following the physical trauma, and (iii) a burn wound, wherein the CD34⁻ stem cells are introduced into the subject's bloodstream immediately following the physical trauma.

In the above methods employing non-genetically modified CD34⁻ stem cells, the subject treated can be any subject. In the preferred embodiment, the subject is human. Furthermore, in the subject methods employing non-genetically modified CD34⁻ stem cells, the CD34⁻ stem cells can be allogenic, autologous or xenogenic with respect to the subject, unless stated or implied otherwise.

This invention provides a method for treating a subject afflicted with a tumor comprising introducing into the subject's bloodstream a therapeutically effective number of genetically modified CD34⁻ stem cells, wherein (a) each of the genetically modified CD34⁻ stem cells contains an exogenous nucleic acid comprising (i) a cytotoxic protein-encoding region operably linked to (ii) a promoter or promoter/enhancer combination, whereby the cytotoxic protein is selectively expressed when the genetically modified CD34⁻ stem cells come into proximity with, and differentiate in proximity with, tumor tissue undergoing angiogenesis, and (b) the introduction of the genetically modified CD34⁻ stem cells is not preceded, accompanied or followed by myeloablation.

All tumor types are envisioned for this method including, for example, a prostate tumor, a pancreatic tumor, a squamous cell carcinoma, a breast tumor, a melanoma, a basal cell carcinoma, a hepatocellular carcinoma, testicular cancer, a neuroblastoma, a glioma or a malignant astrocytic tumor such as glioblastma multiforme, a colorectal tumor, an endometrial carcinoma, a lung carcinoma, an ovarian tumor, a cervical tumor, an osteosarcoma, a rhabdo/leiomyosarcoma, a synovial sarcoma, an angiosarcoma, an Ewing sarcoma/PNET and a malignant lymphoma.

Numerous promoter/enhancer combinations and cytotoxic proteins are also envisioned for this method. In one embodiment, the promoter/enhancer combination is the Tie2 promoter/enhancer, the cytotoxic protein is Herpes simplex viral thymidine kinase, and the subject is treated with ganciclovir in a manner permitting the Herpes simplex viral thymidine kinase to render the ganciclovir cytotoxic. Ganciclovir and its methods of use are well known in the art.

This invention further provides a method for treating a subject afflicted with a gastrointestinal disorder comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which enhances endothelial cell growth, which region is operably linked to (ii) an endothelium-specific promoter or promoter/enhancer combination, (b) the introduction of the genetically modified CD34⁻ stem cells is not preceded, accompanied or followed by myeloablation, and (c) the gastrointestinal disorder is characterized by a need for cell proliferation in the gastrointestinal endothelium.

In this method, the gastrointestinal disorder is preferably colitis, ulcerative colitis, inflammatory bowel disorder or Crohn's disease.

Numerous promoter/enhancer combinations and endothelial cell growth-enhancing proteins are envisioned for this method. In one embodiment, the promoter/enhancer combination is the Tie2 promoter/enhancer and the protein which enhances endothelial cell growth is a vascular endothelial growth factor (VEGF). Other angiogenic factors in addition to VEGF are also envisioned, such as HIF-1a and Carboanhydrase IX.

This invention further provides a method for treating a diabetic subject or a pre-diabetic subject comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which enhances endothelial cell growth, which region is operably linked to (ii) an endothelium-specific promoter or promoter/enhancer combination, and (b) the introduction of the genetically modified CD34⁻ stem cells is not preceded, accompanied or followed by myeloablation.

In one embodiment of this method, the subject is pre-diabetic, either for type I diabetes or type II diabetes. In another embodiment, the subject is diabetic, afflicted either with type I diabetes or type II diabetes.

Numerous promoter/enhancer combinations and endothelial cell growth-enhancing proteins are envisioned for this method. In one embodiment, the promoter/enhancer combination is the Tie2 promoter/enhancer and the protein which enhances endothelial cell growth is a vascular endothelial growth factor (VEGF) associated with angiogenesis.

This invention further provides a method for treating a subject afflicted with muscular dystrophy comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which is absent from or underexpressed in the subject's muscle cells or whose overexpression in the subject's muscle cells is desired, which region is operably linked to (ii) a muscle-specific promoter or muscle-specific promoter/enhancer combination, and (b) the introduction of the genetically modified CD34⁻ stem cells is not preceded, accompanied or followed by myeloablation.

In the preferred embodiment of this method, the subject is afflicted with Duchenne or Becker's muscular dystrophy, and the CD34⁻ stem cells are allogenic or autologous with respect to the subject.

Numerous muscle-specific promoter/enhancer combinations are envisioned for this method. In one embodiment, the muscle-specific promoter/enhancer combination is the MyoD promoter/enhancer. In the preferred embodiment of Duchenne muscular dystrophy, the protein absent from the subject's muscle cells is dystrophin.

This invention further provides a method for improving microcirculation and/or acute wound healing in a subject who is about to undergo, is undergoing or has undergone surgery comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which enhances endothelial cell growth, which region is operably linked to (ii) an endothelium-specific promoter or promoter/enhancer combination, and (b) the introduction of the genetically modified CD34⁻ stem cells is not preceded, accompanied or followed by myeloablation.

This method is appropriate for any type of surgery including, without limitation, abdominal surgery, thoracic surgery, neurosurgery or plastic surgery. Additionally, the surgery can be laproscopic surgery or open surgery.

Numerous promoter/enhancer combinations and endothelial cell growth-enhancing proteins are envisioned for this method. In one embodiment, the promoter/enhancer combination is the Tie2 promoter/enhancer and the protein which enhances endothelial cell growth is a vascular endothelial growth factor (VEGF) associated with angiogenesis.

Finally, this invention provides a method for improving microcirculation and/or acute wound healing in a subject who is about to undergo, is undergoing or has undergone a physical trauma comprising introducing into the subject's bloodstream a therapeutically effective number of genetically modified CD34⁻ stem cells, wherein (a) each of the genetically modified CD34⁻ stem cells contains an exogenous nucleic acid comprising (i) a region encoding a protein which enhances endothelial cell growth, which region is operably linked to (ii) an endothelium-specific promoter or promoter/enhancer combination, and (b) the introduction of the genetically modified CD34⁻ stem cells is not preceded, accompanied or followed by myeloablation.

This method is appropriate for any type of physical trauma. Specifically envisioned are (i) childbirth, (ii) a flesh wound caused by a violent act, wherein the CD34⁻ stem cells are introduced into the subject's bloodstream immediately following the physical trauma, and (iii) a burn wound, wherein the CD34⁻ stem cells are introduced into the subject's bloodstream immediately following the physical trauma.

Numerous promoter/enhancer combinations and endothelial cell growth-enhancing proteins are envisioned for this method. In one embodiment, the promoter/enhancer combination is the Tie2 promoter/enhancer and the protein which enhances endothelial cell growth is a vascular endothelial growth factor (VEGF) associated with angiogenesis.

In the above methods employing genetically modified CD34⁻ stem cells, the subject treated can be any subject. In the preferred embodiment, the subject is human. Furthermore, in the subject methods employing genetically modified CD34⁻ stem cells, the CD34⁻ stem cells can be allogenic, autologous or xenogenic with respect to the subject, unless stated or implied otherwise.

In the instant methods employing genetically modified CD34⁻ stem cells, the exogenous genes are expressed, i.e., "turned on", when the stem cells (i) come into proximity with the appropriate cells in target tissue, (ii) differentiate, and/or (iii) fuse with the appropriate cells in target tissue.

The various proteins and regulatory sequences used in this invention can be readily obtained by one skilled in the art. For example, endothelial cell specificity of the Tie2 promoter enhancer is shown in Schlaeger T M, Bartunkova S, Lawitts J A, Teichmann G, Risau W, Deutsch U, Sato T N. Uniform vascular-endothelial-cell-specific gene expression in both embryonic and adult transgenic mice. *Proc Natl Acad Sci USA*. 1997 94:3058-63. The HSV TK-V00467 Herpes gene can be used for thymidine kinase (ATP:thymidine 5' phosphotransferase, e.c. 2.7.1.21) (type 1 strain CL101).

This invention will be better understood by reference to the Experimental Details which follow, but those skilled in the art will readily appreciate that the specific experiments detailed are only illustrative of the invention as described more fully in the claims which follow thereafter.

Experimental Details

Part I

Genetically Engineered Transgenic CD34-Negative Stem Cells for Therapeutic Gene Delivery Synopsis Stem cell and gene therapy approaches hold much hope for the development of new tools to treat many life-threatening diseases. The linking of stem cell therapy with selective gene therapy enhances therapeutic options for the regeneration or replacement of diseased or missing cells. Tissue-specific gene expression in the context of differentiation of CD34-negative, in-vitro adherent growing stem cells are used to generate transgenic CD34-negative progenitor cells, which will lead to selectivity of cells and inducibility of gene expression also for safety reasons. Viral and non-viral genes delivering technologies are detailed as are techniques for the modulation of gene expression in the context of stem cell recruitment and differentiation. Potential clinical applications for this new therapeutic strategy are described, brining the transgenic progenitor cells to the cancer or site of tissue regeneration to induce anti-tumor therapy or promote tissue remodeling and wound healing. Transgenic progenitor cells serve as potent gene delivery vehicle.

Stem Cells as Gene Delivery Vehicles

Stem cells offer the potential to provide cellular therapies for diseases that are refractory to other treatments. For each type of stem cell the ultimate goal is the same: the cell should express a specific repertoire of genes, thereby modifying cell identity to maintain, replace, or rescue a particular tissue. To help support differentiation in the specific tissue environment attempts are being made to modify the "nuclear programming" of stem cells.

Multipotent stem cells, mesenchymal stem cells and multipotent adult progenitor cells (MAPCs) represent promising stem cell populations as they are capable of differentiating along different lineages. They represent the "cellular engines" that drive the renewal of adult mammalian tissues. These cells divide continuously throughout life to produce new progeny cells that undergo a program of differentiation and maturation to replace older expired tissue cells. The same cell turnover program is thought in some cases to provide a source of cells for the repair and regeneration of adult tissues. The regenerative potential of the different stem cell types underlies the current interest in adapting these cells for applications in cell replacement therapy.

Potential sources of stem cells for therapy include bone marrow, peripheral blood, CNS, liver, pancreas, muscle, skin lung, intestine heart and fat (Koerbling M, Estrov Z, *Adult stem cells for tissue repair—a new therapeutic concept*?) *NEJM* 2003 349: 570-582). For clinical application the sources of stem cells should be easily accessible and readily harvested with minimal risk to the patient and provide abundant cells. In this regard fat tissue represents a promising tissue source. (*Adipose derived stem cells for the regeneration of damaged tissue* Parker M, Adam K, *Expert Opion Biol Therap*, 2006, 567-568) Adipose derived stem cells and bone marrow derived stem cells share similar growth kinetics, characteristics regarding cell senescence, gene transduction efficiency, CD surface marker expression and gene transcription profiles (*Cells Tissues Organs.* 2003; 174 (3):101-9. *Comparison of multi-lineage cells from human adipose tissue and bone marrow*. De Ugarte D A, Morizono K, Elbarbary A, Alfonso Z, Zuk P A, Zhu M, Dragoo J L, Ashjian P, Thomas B, Benhaim P, Chen I, Fraser J, Hedrick M H, Mol Biol Cell. 2002 December; 13 (12):4279-95. *Human adipose tissue is a source of multipotent stem cells*. Zuk P A, Zhu M, Ashjian P, De Ugarte D A, Huang J I, Mizuno H, Alfonso Z C, Fraser J K, Benhaim P, Hedrick M H).

Stem cells derived from different sources are also being evaluated as potential vehicles for cell and gene specific therapy against disease. Their high self-renewal potential makes them promising candidates for the restoration or replacement of organ systems and/or the delivery of gene products. While progenitor cells may show good proliferation and differentiation potential in vitro, their biological properties in vivo remain to be defined. Stem cells expanded in vitro represent heterogeneous populations that include multiple generations of mesenchymal (stromal) cell progeny, which lack the expression of most differentiation markers like CD34. These populations may have retained a limited proliferation potential and responsiveness for terminal differentiation and maturation along mesenchymal and non-mesenchymal lineages. Hopefully in the future better markers for multipotent stem cell populations will improve the ability to distinguish these stem cells from other progenitor cell populations.

Tissue-Specific Promoters Used to Deliver Therapeutic Gene Expression in the Correct Biological Context.

Stem-cell-mediated therapy ultimately entails nuclear reprogramming—the alteration of gene expression patterns unique to cell types in diverse tissues and organs. In a number of inherited stem cell diseases, a genetic defect imparts a survival disadvantage to the affected stem cell population. In these diseases, the transplantation of a "corrected" stem cell population is thought to undergo spontaneous in vivo selection in the absence of any exogenously applied selective pressure. For example, in X-linked SCID the introduction of a therapeutic transgene confers a continuous proliferation and survival advantage to the transduced cell population (Neff et al., 2006). However, similar in vivo selection effects are usually not directly possible in a majority of diseases. In settings where an over expression of the therapeutic gene does not confer a survival advantage, a second selectable gene, ideally under pharmacological regulation, can be incorporated into the vector. (Tirona and Kim, 2005). Systems that allow for pharmacologically regulated selection include reversible forced protein-protein interaction using so called "chemical inducers of dimerization" (CIDs). These systems rely on two components. The first is a ligand or drug, and the second is a fusion protein that combines a ligand-binding protein domain and an effector domain (usually the intracellular proportion of a growth factor receptor). The effector domain is activated by drug binding leading to protein dimerization. The signaling fusion thus serves as a switch that is turned on in the presence of the CID and off following withdrawal of the CID. The incorporation of systems like this into a stem cell population can allow a drug-dependent control of proliferation of the transduced cell population (Neff et al., 2006; Neff and Blau, 2001).

The use of stem cells as delivery vehicles for therapeutic genes can be seen to offer a series of advantages. Stem cells are often actively recruited to damaged tissues where they undergo differentiation during tissue repair. For example CD34+ bone marrow-derived progenitor cells contribute to tissue repair by differentiating into endothelial cells, vascular smooth muscle cells, hematopoietic cells, and possibly other cell types. However, the mechanisms by which circulating progenitor cells home to remodeling tissues remain unclear. Jin et al. have demonstrated that integrin $\alpha 4\beta 1$ (VLA-4) can promote the homing of circulating progenitor cells to the $\alpha 4\beta 1$ ligands VCAM and cellular fibronectin expressed on actively remodeling neovasculature. Progenitor cells which express integrin α4β1 were shown to home to sites of active tumor neovascularization but not to normal tissues. Antagonists of integrin α4β1, but not other integrins, blocked the adhesion of these cells to endothelia and outgrowth into differentiated cell types. (Jin et al, 2006)

In addition to integrins, chemokines and their receptors also appear to play central roles in the tissue-specific homing of stem cells. On the basis of their chemokine receptor expression profile, CD34⁻ MSCs were predicted to home to secondary lymphatic organs (CCR7), skin (CCR4, CCR10), small intestine (CCR10), and salivary glands (CCR10). After transiently labeling CD34– MSC with CMFDA or stably introducing green fluorescent protein (GFP) expression plasmids, the cells were injected into syngeneic healthy mice and the tissue distribution of the cells determined one three and seven days latter. Interestingly, the stem cells did not home back to the bone marrow but were found to migrate to secondary lymphatic organs, salivary glands, intestine and skin in accordance with their chemokine receptor expression profile.

Given that stem cells can show a selective migration to different tissue microenvironments in normal as well as diseased settings, the use of tissue-specific promoters linked to the differentiation pathway initiated in the recruited stem cell could in theory be used to drive the selective expression of therapeutic genes only within a defined biologic context. Stem cells that are recruited to other tissue niches, but do not undergo the same program of differentiation, should not express the therapeutic gene. This approach allows a significant degree of potential control for the selective expression of the therapeutic gene within a defined microenvironment and has been successfully applied to regulate therapeutic gene expression during neovascularization.

A large number of promoters have been characterized for their tissue-specific expression. A good source for this information can be found in the transgene literature, or for example in the various databases that list tissue-specific promoter activity for the expression of the CRE transgenes used to drive tissue-specific CRE/Lox targeted gene deletion models in mouse (for example: http://www.mshri.on.ca/nagy/Creworks.htm). Promoters can be introduced that are selectively regulated in the context of inflammation or neovascularization. In this regard the Tie2-promoter, Flk1 promoter and intronic enhancer, endothelin-1 promoter and the pre-proendothelin-1 promoter have been studied for endothelial specific expression (Huss et al., 2004). The application of specific reporter genes and new imaging techniques can be used to define the tissue-specific expression of the candidate promoter within the context of stem cell transplantation. Other options regarding the delivery of genes include the application of an internal ribosome entry site (IRES) signal for the expression of multiple genes from a single promoter (Jackson, 2005), for example, a therapeutic gene in conjunction with a reporter gene can be used to better follow the distribution of expression of the therapeutic gene in an experimental context.

Importantly, many promoters can show "leakage" of expression in other tissue types or a low level basal expression in the engineered cells. Promoter engineering is a new technology that can allow one to "tune" promoter specificity to limit cross tissue activity thus allowing a more restrictive expression to specific cell types (Fessele et al., 2002; Werner et al., 2003).

Gene Delivery Methods

The various gene delivery methods currently being applied to stem cell engineering include viral and non viral vectors, as well as biological or chemical methods of transfection. The methods can yield either stable or transient gene expression in the system used.

Viral Gene Delivery Systems

Because of their high efficiency of transfection, genetically modified viruses have been widely applied for the delivery of genes into stem cells.

DNA Virus Vectors (i) Adenovirus

Adenoviruses are double stranded, nonenveloped and icosahedral viruses containing a 36 kb viral genome (Kojaoghlanian et al., 2003). Their genes are divided into early (E1A, E1B, E2, E3, E4), delayed (IX, IVa2) and major late (L1, L2, L3, L4, L5) genes depending on whether their expression occurs before or after DNA replication. To date, 51 human adenovirus serotypes have been described which can infect and replicate in a wide range of organs. The viruses are classified into the following subgroups: A—induces tumor with high frequency and short latency, B—are weakly oncogenic, and C—are non-oncogenic (Cao et al., 2004; Kojaoghlanian et al., 2003).

These viruses have been used to generate a series of vectors for gene transfer cellular engineering. The initial generation of adenovirus vectors were produced by deleting the E1 gene (required for viral replication) generating a vector with a 4 kb cloning capacity. An additional deletion of E3 (responsible for host immune response) allowed an 8 kb cloning capacity (Bett et al., 1994; Danthinne and Imperiale, 2000; Danthinne and Werth, 2000). The second generation of vectors was produced by deleting the E2 region (required for viral replication) and/or the E4 region (participating in inhibition of host cell apoptosis) in conjunction with E1 or E3 deletions. The resultant vectors have a cloning capacity of 10-13 kb (Armentano et al., 1995). The third "gutted" generation of vectors was produced by deletion of the entire viral sequence with the exception of the inverted terminal repeats (ITRs) and the cis acting packaging signals. These vectors have a cloning capacity of 25 kb (Kochanek et al., 2001) and have retained their high transfection efficiency both in quiescent and dividing cells.

Importantly, the adenovirus vectors do not normally integrate into the genome of the host cell, but they have shown efficacy for transient gene delivery into adult stem cells. These vectors have a series of advantages and disadvantages. An important advantage is that they can be amplified at high titers and can infect a wide range of cells (Benihoud et al., 1999; Kanerva and Hemminki, 2005). The vectors are generally easy to handle due to their stability in various storing conditions. Adenovirus type 5 (Ad5) has been successfully used in delivering genes in human and mouse stem cells (Smith-Arica et al., 2003). The lack of adenovirus integration into host cell genetic material can in many instances be seen as a disadvantage, as its use allows only transient expression of the therapeutic gene.

For example in a study evaluating the capacity of mesenchymal stem cells to undergo chondrogenesis when TGF-beta1 and bone morphogencic protein-2 (BMP-2) were delivered by adenoviral-mediated expression, the chondrogenesis was found to closely correlated with the level and duration of the transiently expressed proteins. Transgene expression in all aggregates was highly transient, showing a marked decrease after 7 days. Chondrogenesis was inhibited in aggregates modified to express >100 ng/ml TGF-beta1 or BMP-2; however, this was partly due to the inhibitory effect of exposure to high adenoviral loads (*Mol. Ther.* 2005 August; 12 (2):219-28. *Gene-induced chondrogenesis of primary mesenchymal stem cells in vitro.* Palmer G D, Steinert A, Pascher A, Gouze E, Gouze J N, Betz O, Johnstone B, Evans C H, Ghivizzani S C). In a second model using rat adipose derived stem cells transduced with adenovirus carrying the recombinant human bone morphogenic protein-7 (BMP-7) gene showed promising results for an autologous source of stem cells for BMP gene therapy. However, activity assessed by measuring alkaline phosphatase in vitro was transient and peaked on day 8. Thus the results were similar to those found in the chondrogenesis model (*Cytotherapy.* 2005; 7 (3):273-81).

Thus for therapies or experiments that do not require stable gene expression adenovirus vectors may be a good option. An additional important problem in using adenovirus vectors is that they can elicit a strong immune response directed against the engineered cells upon transfer into the host. Clearly this may be important issue when considering the application of engineered cells in a therapeutic setting (J. N. Glasgow et al., *Transductional and transcriptional targeting of adenovirus for clinical applications. Curr Gene Ther.* 2004 March; 4 (1):1-14). In vitro and in vivo induction of bone formation based on ex vivo gene therapy using rat adipose-derived adult stem cells expressing BMP-7, Yang M, Ma Q J, Dang G T, Ma K, Chen P, Zhou C Y).

Adenovirus vectors based on Ad type 5 have been shown to efficiently and transiently introduce an exogenous gene via the primary receptor, coxsackievirus, and adenovirus receptor (CAR). However, some kinds of stem cells, such as MSC and hematopoietic stem cells, apparently cannot be efficiently transduced with conventional adenovirus vectors based on Ad serotype 5 (Ad5), because of the lack of CAR expression. To overcome this problem, fiber-modified adenovirus vectors and an adenovirus vector based on another serotype of adenovirus have been developed. (*Mol. Pharm.* 2006 March-April; 3 (2):95-103. Adenovirus vector-mediated gene transfer into stem cells. Kawabata K, Sakurai F, Koizumi N, Hayakawa T, Mizuguchi H. Laboratory of Gene Transfer and Regulation, National Institute of Biomedical Innovation, Osaka 567-0085, Japan).

(ii) Adeno-Associated Virus

Adeno-Associated viruses (AAV) are ubiquitous, noncytopathic, replication-incompetent members of ssDNA animal virus of parvoviridae family (G. Gao et al., *New recombinant serotypes of AAV vectors. Curr Gene Ther.* 2005 June; 5 (3):285-97). AAV is a small icosahedral virus with a 4.7 kb genome. These viruses have a characteristic termini consisting of palindromic repeats that fold into a hairpin. They replicate with the help of helper virus, which are usually one of the many serotypes of adenovirus. In the absence of helper virus they integrate into the human genome at a specific locus (AAVS1) on chromosome 19 and persist in latent form until helper virus infection occurs (Atchison et al., 1965, 1966). AAV can transduce cell types from different species including mouse, rat and monkey. Among the serotypes, AAV2 is the most studied and widely applied as a gene delivery vector. Its genome encodes two large opening reading frames (ORFs) rep and cap. The rep gene encodes four proteins Rep 78, Rep 68, Rep 52 and Rep 40 which play important roles in various stages of the viral life cycle (e.g. DNA replication, transcriptional control, site specific integration, accumulation of single stranded genome used for viral packaging). The cap gene encodes three viral capsid proteins VP1, VP2, VP3 (Becerra et al., 1988; Buning et al., 2003). The genomic 3' end serves as the primer for the second strand synthesis and has terminal resolution sites (TRS) which serve as the integration sequence for the virus as the sequence is identical to the sequence on chromosome 19 (Young and Samulski, 2001; Young et al., 2000).

These viruses are similar to adenoviruses in that they are able to infect a wide range of dividing and non-dividing cells. Unlike adenovirus, they have the ability to integrate into the host genome at a specific site in the human genome. Unfortunately, due to their rather bulky genome, the AAV vectors have a limited capacity for the transfer of foreign gene inserts (Wu and Ataai, 2000).

RNA Virus Vectors (i) Retroviruses

Retroviral genomes consist of two identical copies of single stranded positive sense RNAs, 7-10 kb in length coding for three genes; gag, pol and env, flanked by long terminal repeats (LTR) (Yu and Schaffer, 2005). The gag gene encodes the core protein capsid containing matrix and nucleocapsid elements that are cleavage products of the gag precursor protein. The pol gene codes for the viral protease, reverse transcriptase and integrase enzymes derived from gag-pol precursor gene. The env gene encodes the envelop glycoprotein which mediates viral entry. An important feature of the retroviral genome is the presence of LTRs at each end of the genome. These sequences facilitate the initiation of viral DNA synthesis, moderate integration of the proviral DNA into the host genome, and act as promoters in regulation of viral gene transcription. Retroviruses are subdivided into three general groups: the oncoretroviruses (Maloney Murine Leukenmia Virus, MoMLV), the lentiviruses (HIV), and the spumaviruses (foamy virus) (Trobridge et al., 2002).

Retroviral based vectors are the most commonly used integrating vectors for gene therapy. These vectors generally have a cloning capacity of approximately 8 kb and are generated by a complete deletion of the viral sequence with the exception of the LTRs and the cis acting packaging signals.

The retroviral vectors integrate at random sites in the genome. The problems associated with this include potential insertional mutagenesis, and potential oncogenic activity driven from the LTR. The U3 region of the LTR harbors promoter and enhancer elements, hence this region when deleted from the vector leads to a self-inactivating vector where LTR driven transcription is prevented. An internal promoter can then be used to drive expression of the transgene.

The initial studies of stem cell gene transfer in mice raised the hope that gene transfer into humans would be equally as efficient (O'Connor and Crystal, 2006). Unfortunately gene transfer using available retroviral vector systems to transfect multi-lineage long-term repopulating stem cells is still significantly more efficient in the mouse. The reduced efficacy of gene transfer in humans, as well as the uncontrolled integration of the retroviral vector represents important hurdles for the application of these vectors as a treatment modality in the context of stem cell engineering.

(ii) Lentivirus

Lentiviruses are members of Retroviridae family of viruses (M. Scherr et al., *Gene transfer into hematopoietic stem cells using lentiviral vectors. Curr Gene Ther.* 2002 February; 2 (1):45-55). They have a more complex genome and replication cycle as compared to the oncoretroviruses (Beyer et al., 2002). They differ from simpler retroviruses in that they possess additional regulatory genes and elements, such as the tat gene, which mediates the transactivation of viral transcription (Sodroski et al., 1996) and rev, which mediates nuclear export of unspliced viral RNA (Cochrane et al., 1990; Emerman and Temin, 1986).

Lentivirus vectors are derived from the human immunodeficiency virus (HIV-1) by removing the genes necessary for viral replication rendering the virus inert. Although they are devoid of replication genes, the vector can still efficiently integrate into the host genome allowing stable expression of the transgene. These vectors have the additional advantage of a low cytotoxicity and an ability to infect diverse cell types. Lentiviral vectors have also been developed from Simian, Equine and Feline origin but the vectors derived from Human Immunodeficiency Virus (HIV) are the most common (Young et al., 2006).

Lentivirus vectors are generated by deletion of the entire viral sequence with the exception of the LTRs and cis acting packaging signals. The resultant vectors have a cloning capacity of about 8 kb. One distinguishing feature of these vectors from retroviral vectors is their ability to transduce dividing and non-dividing cells as well as terminally differentiated cells (Kosaka et al., 2004). The lentiviral delivery system is capable of high infection rates in human mesenchymal and embryonic stem cells. In a study by Clements et al., the lentiviral backbone was modified to express mono- and bi-cistronic transgenes and was also used to deliver short hairpin ribonucleic acid for specific silencing of gene expression in human stem cells. (*Tissue Eng.* 2006 July; 12 (7): 1741-51. *Lentiviral manipulation of gene expression in human adult and embryonic stem cells*. Clements M O, Godfrey A, Crossley J, Wilson S J, Takeuchi Y, Boshoff C).

Table 1 summarizes the viral vectors described above.

2000). This system directs the precise transfer of specific constructs from a donor plasmid into a mammalian chromosome. The excision and integration of the transposon from a plasmid vector into a chromosomal site is mediated by the SB transposase, which can be delivered to cells as either in a cis or trans manner (Kaminski et al., 2002). A gene in a chromosomally integrated transposon can be expressed over the lifetime of a cell. SB transposons integrate randomly at TA-dinucleotide base pairs although the flanking sequences can influence integration. While the results to date do not suggest that random insertions of SB transposons represent the same level of risks seen with viral vectors, more data are required before the system can be safely applied to human trials.

Physical Methods to Introduce Vectors into Cells (i) Electroporation

Electroporation relies on the use of brief, high voltage electric pulses which create transient pores in the membrane by overcoming its capacitance. One advantage of this method is that it can be utilized for both stable and transient gene expression in most cell types. The technology relies on the relatively weak nature of the hydrophobic and hydrophilic interactions in the phospholipid membrane and its ability to recover its original state after the disturbance. Once the mem-

| Vector | Insert capacity(kb) | Tropism | Vector genome form | Expression | Inflammatory potential | Efficiency |
|---|---|---|---|---|---|---|
| Enveloped | | | | | | |
| Retrovirus | 8 | Dividing cells only | Integrated | Stable | Low | High |
| Lentivirus | 8 | Dividing and non-dividing | Integrated | Stable | Low | High |
| Non-enveloped | | | | | | |
| Adeno-associated virus | <5 | Dividing and non-dividing | Episomal and integrated | Stable | Low | High |
| Adenovirus | 4-25 | Dividing and non-dividing | Episomal | Transient | High | High |

Non-Viral Gene Delivery Systems (i) Methods for the Facilitated Integration of Genes In addition to the viral based vectors discussed above, other vector systems that lack viral sequence are currently under development. The alternative strategies include conventional plasmid transfer and the application of targeted gene integration through the use of integrase or transposase technologies. These represent important new approaches for vector integration and have the advantage of being both efficient, and often site specific in their integration. Currently three recombinase systems are available for genetic engineering: cre recombinase from phage P1 (Lakso et al., 1992; Orban et al., 1992), FLP (flippase) from yeast 2 micron plasmid (Dymecki, 1996; Rodriguez et al., 2000), and an integrase isolated from streptomyses phage ΦC31 (Ginsburg and Calos, 2005). Each of these recombinases recognize specific target integration sites. Cre and FLP recombinase catalyze integration at a 34 bp palindromic sequence called lox P (locus for crossover) and FRT (FLP recombinase target) respectively. Phage integrase catalyzes site-specific, unidirectional recombination between two short att recognition sites in mammalian genomes. Recombination results in integration when the att sites are present on two different DNA molecules and deletion or inversion when the att sites are on the same molecule. It has been found to function in tissue culture cells (in vitro) as well as in mice (in vivo).

The Sleeping Beauty (SB) transposon is comprised of two inverted terminal repeats of 340 base pairs each (Izsvak et al., brane is permeabilized, polar molecules can be delivered into the cell with high efficiency. Large charged molecules like DNA and RNA move into the cell through a process driven by their electrophoretic gradient. The amplitude of the pulse governs the total area that would be permeabilized on the cell surface and the duration of the pulse determines the extent of permeabilization (Gabriel and Teissie, 1997). The permeabilized state of the cell depends on the strength of the pulses. Strong pulses can lead to irreversible permeabilization, irreparable damage to the cell and ultimately cell death. For this reason electroporation is probably the harshest of gene delivery methods and it generally requires greater quantities of DNA and cells. The effectiveness of this method depends on many crucial factors like the size of the cell, replication and temperature during the application of pulse (Rols and Teissie, 1990).

The most advantageous feature of this technique is that DNA can be transferred directly into the nucleus increasing its likelihood of being integrated into the host genome. Even cells difficult to transfect can be stably transfected using this method (Aluigi et al., 2005; Zernecke et al., 2003). Modification of the transfection procedure used during electroporation has led to the development of an efficient gene transfer method called nucleofection. The Nucleofector™ technology, is a non-viral electroporation-based gene transfer technique that has been proven to be an efficient tool for transfecting hard-to-transfect cell lines and primary cells including MSC (Michela Aluigi, *Stem Cells* Vol. 24, No. 2, February 2006, pp. 454-461).

Biomolecule-Based Methods (i) Protein Transduction Domains (PTD)

PTD are short peptides that are transported into the cell without the use of the endocytotic pathway or protein channels. The mechanism involved in their entry is not well understood, but it can occur even at low temperature (Derossi et al. 1996). The two most commonly used naturally occurring PTDs are the trans-activating activator of transcription domain (TAT) of human immunodeficiency virus and the homeodomain of Antennapedia transcription factor. In addition to these naturally occurring PTDs, there are a number of artificial peptides that have the ability to spontaneously cross the cell membrane (Joliot and Prochiantz, 2004). These peptides can be covalently linked to the pseudo-peptide backbone of PNA (peptide nucleic acids) to help deliver them into the cell.

(ii) Liposomes

Liposomes are synthetic vesicles that resemble the cell membrane. When lipid molecules are agitated with water they spontaneously form spherical double membrane compartments surrounding an aqueous center forming liposomes. They can fuse with cells and allow the transfer of "packaged" material into the cell. Liposomes have been successfully used to deliver genes, drugs, reporter proteins and other biomolecules into cells (Felnerova et al., 2004). The advantage of liposomes is that they are made of natural biomolecules (lipids) and are nonimmunogenic.

Diverse hydrophilic molecules can be incorporated into them during formation. For example, when lipids with positively charged head group are mixed with recombinant DNA they can form lipoplexes in which the negatively charged DNA is complexed with the positive head groups of lipid molecules. These complexes can then enter the cell through the endocytotic pathway and deliver the DNA into lysosomal compartments. The DNA molecules can escape this compartment with the help of dioleoylethanolamine (DOPE) and are transported into the nucleus where they can be transcribed (Tranchant et al., 2004).

Despite their simplicity, liposomes suffer from low efficiency of transfection because they are rapidly cleared by the reticuloendothelial system due to adsorption of plasma proteins. Many methods of stabilizing liposomes have been used including modification of the liposomal surface with oligosaccharides, thereby sterically stabilizing the liposomes (Xu et al., 2002).

(iii) Immunoliposomes

Immunoliposomes are liposomes with specific antibodies inserted into their membranes. The antibodies bind selectively to specific surface molecules on the target cell to facilitate uptake. The surface molecules targeted by the antibodies are those that are preferably internalized by the cells so that upon binding, the whole complex is taken up. This approach increases the efficiency of transfection by enhancing the intracellular release of liposomal components. These antibodies can be inserted in the liposomal surface through various lipid anchors or attached at the terminus of polyethylene glycol grafted onto the liposomal surface. In addition to providing specificity to gene delivery, the antibodies can also provide a protective covering to the liposomes that helps to limit their degradation after uptake by endogenous RNAses or proteinases (Bendas, 2001). To further prevent degradation of liposomes and their contents in the lysosomal compartment, pH sensitive immunoliposomes can be employed (Torchilin, 2006). These liposomes enhance the release of liposomal content into the cytosol by fusing with the endosomal membrane within the organelle as they become destabilized and prone to fusion at acidic pH.

In general non-viral gene delivery systems have not been as widely applied as a means of gene delivery into stem cells as viral gene delivery systems. However, promising results were demonstrated in a study looking at the transfection viability, proliferation and differentiation of adult neural stem/progenitor cells into the three neural lineages neurons. Non-viral, non-liposomal gene delivery systems (ExGen500 and FuGene6) had a transfection efficiency of between 16% (ExGen500) and 11% (FuGene6) of cells. FuGene6-treated cells did not differ from untransfected cells in their viability or rate of proliferation, whereas these characteristics were significantly reduced following ExGen500 transfection. Importantly, neither agent affected the pattern of differentiation following transfection. Both agents could be used to genetically label cells, and track their differentiation into the three neural lineages, after grafting onto ex vivo organotypic hippocampal slice cultures (*J Gene Med.* 2006 January; 8 (1): 72-81. *Efficient non-viral transfection of adult neural stem/progenitor cells, without affecting viability, proliferation or differentiation.* Tinsley R B, Faijerson J, Eriksson P S).

(iv) Polymer-Based Methods

The protonated $\epsilon$-amino groups of poly L-lysine (PLL) interact with the negatively charged DNA molecules to form complexes that can be used for gene delivery. These complexes can be rather unstable and showed a tendency to aggregate (Kwoh et al., 1999). The conjugation of polyethylene glycol (PEG) was found to lead to an increased stability of the complexes (Lee et al., 2005, Harada-Shiba et al., 2002). To confer a degree of tissue-specificity, targeting molecules such as tissue-specific antibodies have also been employed (Trubetskoy et al., 1992, Suh et al., 2001).

An additional gene carrier that has been used for transfecting cells is polyethylenimine (PEI) which also forms complexes with DNA. Due to the presence of amines with different pKa values, it has the ability to escape the endosomal compartment (Boussif et al., 1995). PEG grafted onto PEI complexes was found to reduce the cytotoxicity and aggregation of these complexes. This can also be used in combination with conjugated antibodies to confer tissue-specificity (Mishra et al., 2004, Shi et al., 2003, Chiu et al., 2004, Merdan et al., 2003).

Implications for Medicine

Stem cells not only have the ability to differentiate into diverse tissues, but due to their inherent ability to home to damaged tissue, they have the potential to deliver the expression of therapeutic genes to specific tissue environments. Through the use of molecular engineering approaches, stem cells can be used as vehicles to selectively express genes in areas of defects or need, thereby releasing the therapeutic product of the transfection only where it is required. Diseases where genetically engineered stem cells might play a role in future are those where a protein or an entire enzyme is missing or nonfunctional or where certain factors provide improved function in a specific tissue.

A series of studies using stem cells in therapeutic settings have been already been conducted for the treatment of a diverse range of diseases that include cancer, neurodegenerative disorders such as Parkinson's disease or Alzheimer's disease, ischemic disease of the heart, and muscle dystrophies.

The transfer of drug resistance genes into hematopoietic stem cells shows promise for the treatment of a variety of inherited diseases. These include; X-linked severe combined immune deficiency, adenosine deaminase deficiency, thalassemia.

The combined stem cell and gene therapy approach has the potential for being tailored for acquired disorders such as breast cancer, lymphomas, brain tumors, and testicular cancer. In this regard, studies using the combined approach for the treatment of cancer have been initiated. These studies range from improving the drug resistance of transplanted hematopoietic stem cells to using genetically modified stem cells to target cancer.

Drug resistance genes have been transferred into hematopoietic stem cells for providing myeloprotection against chemotherapy-induced myelosuppression or for selecting hematopoietic stem cells that are concomitantly transduced with another gene for correction of an inherited disorder. (*Cancer Gene Ther.,* 2005 November; 12 (11):849-63. *Hematopoietic stem cell gene therapy with drug resistance genes: an update*. Budak-Alpdogan T, Banerjee D, Bertino J R).

Examples of using stem cells to target cancer include the enhancement of bystander effect-mediated gene therapy using genetically engineered neural stem cells for the treatment of gliomas, and using hematopoietic stem cells carrying the gene of ribonuclease inhibitor to target the vasculature of melanomas.

An additional approach for cancer makes use of the ability of stem cells to be recruited to tumor vasculature and to differentiate into endothelial-like cells. Depending upon the tumor type, approximately 30% of new vascular endothelial cells in tumors can be derived from bone marrow progenitors (Hammerling and Ganss, 2006). Thus, the use of genetically modified progenitor cells recruited from the peripheral circulation may represent a potential vehicle for gene therapy of tumors (Reyes et al., 2002). The Herpes simplex virus 1 (HSV) thymidine kinase (tk) suicide gene together with ganciclovir (GCV) have been successfully used for the in vivo treatment of various solid tumors (Dancer et al., 2003; Pasanen et al., 2003). The selective expression of HSV-tk by endothelial cells during neovascularization in combination with tk modification of GCV leads to a lethal environment for proliferating cells. A series of promoters have been identified that are induced during neovascularization allowing the selective activation of the suicide gene following the recruitment and differentiation of engineered precursor cells.

A "bystander effect" is described as the ability of cells to mediate cell damage to distant cells. In a recent study by Li et al. the bystander effect of neural stem cells transduced with the HSV-tk gene (NSCtk) on rat glioma cells was examined. Intracranial co-implantation experiments in athymic nude mice or Sprague-Dawley rats, showed that the animals co-implanted with NSCtk and glioma cells and then treated with ganciclovir (GCV) showed no intracranial tumors and survived more than 100 days, while those treated with physiological saline (PS) died of tumor progression. (*Cancer Gene Ther.,* 2005 July; 12(7):600-7. *Bystander effect-mediated gene therapy of gliomas using genetically engineered neural stem cells*. Li S, Tokuyama T, Yamamoto J, Koide M, Yokota N, Namba H).

Human ribonuclease inhibitor (hRI) can inhibit the activity of pancreatic RNase (RNase A) and it has been suggested that RI may act as a latent antiangiogenic agent. Fu et al. examined the feasibility of transfecting the RI gene into murine hematopoietic cells and then inducing expression to block angiogenesis in solid tumors. RI from human placenta was cloned and inserted into the retroviral vector pLNCX. Murine bone marrow hematopoietic cells were then infected with the pLNCX-RI retroviral vector. Infected cells were then injected into lethally irradiated mice. After administration of hematopoietic cells carrying the RI gene, the mice were implanted with B16 melanomas and the tumor was grown for 21 days. Tumors from the control groups became large and well vascularized. In contrast, tumors from mice treated with hematopoietic cells carrying the RI gene were small and possessed a relatively low density of blood vessels. (*Cancer Gene Ther.* 2005 March; 12 (3):268-75. *Anti-tumor effect of hematopoietic cells carrying the gene of ribonuclease inhibitor*. Fu P, Chen J, Tian Y, Watkins T, Cui X, Zhao B).

Many studies that focus on Parkinson's disease use either cell transplantation or gene therapy (*Gene Ther.,* 2003 September; 10 (20):1721-7. *Gene therapy progress and prospects: Parkinson's disease*. Burton E A, Glorioso J C, Fink D J). However, few studies to date have combined the two approaches. Liu et al. used bone marrow derived stromal cells to deliver therapeutic genes to the brain. The authors used an adeno-associated virus (AAV) vector to deliver tyrosine hydroxylase (TH) gene to bone marrow stromal cells. MSCs expressing TH gene were then transplanted into the striatum of Parkinson's disease rat. The gene expression efficiency was found to be approximately 75%. Functional improvement in the diseased rats was detected after TH-engineered marrow stromal cells engraftment. Histological examination showed that the TH gene was expressed around the transplantation points, and that the dopamine levels in the lesioned striatum of the rats were higher than in controls. Functional improvement of the animals was observed (*Brain Res Brain Res Protoc.,* 2005 May; 15 (1):46-51. Epub 2005, Apr. 22. *Therapeutic benefit of TH-engineered mesenchymal stem cells for Parkinson's disease*. Lu L, Zhao C, Liu Y, Sun X, Duan C, Ji M, Zhao H, Xu Q, Yang H).

Ischemic cardiovascular disease is an additional target for engineered stem cell therapy. Chen et al., used purified CD34 (+) cells obtained from human umbilical cord blood, transfected with human angiopoietin-1 (Ang1) and VEGF(165) genes using an AAV vector. The engineered cells were injected together with VEGF intramyocardially at the left anterior free wall, which led to decreased infarct size, and significantly increased capillary density after treatment, as well as improved long term cardiac performance measured using echocardiography 4 weeks after myocardial infarction. (*Eur J Clin Invest.,* 2005 November; 35 (11):677-86. *Combined cord blood stem cells and gene therapy enhances angiogenesis and improves cardiac performance in mouse after acute myocardial infarction*. Chen H K, Hung H F, Shyu K G, Wang B W, Sheu J R, Liang Y J, Chang C C, Kuan P).

The muscle dystrophies represent a heterogeneous group of neuromuscular disorders characterized by progressive muscle wasting. To date no adequate treatment modality exists for these patients. Adult stem cell populations, including MSC, as well as embryonic stem cells have been evaluated for their ability to correct the dystrophic phenotype. To date, the described methods have not shown much promise. The reasons described for failure exemplifies the difficulties researchers encounter when using genetically modified stem cells: the underlying mechanism responsible for a myogenic potential in stem cells has not yet been fully elucidated, homing of the donor population to the muscle is often inadequate, and poorly understood immune responses in the recipient can lead to limited treatment success (*Stem cell based therapies to treat muscular dystrophies. Price, Kuroda, Rudnicki*) One approach used for the treatment of Duchenne muscular dystrophy (DMD) utilizes autologous cell transplantation of myogenic stem cells that have been transduced with a therapeutic expression cassette. Development of this method has been hampered by a series of problems including; a low frequency of cellular engraftment, difficulty in tracing transplanted cells, rapid loss of autologous cells carrying marker genes, and difficulty in introducing the stable transfer of the large dystrophin gene into myogenic stem cells.

A mini Dys-GFP fusion gene was engineered by replacing the dystrophin C-terminal domain (DeltaCT) with an eGFP coding sequence and removing much of the dystrophin central rod domain (DeltaH2-R19). In a transgenic mdx(4Cv) mouse expressing the mini Dys-GFP fusion protein under the control of a skeletal muscle-specific promoter, the green fusion protein localized on the sarcolemma, where it assembled the dystrophin-glycoprotein complex and prevented the development of dystrophy in transgenic mdx(4Cv) muscles. (*Hum Mol. Genet.*, 2006 May 15; 15 (10): 1610-22. Epub 2006 Apr. 4. *A highly functional mini-dystrophin/GFP fusion gene for cell and gene therapy studies of Duchenne muscular dystrophy*. Li S, Kimura E, Ng R, Fall B M, Meuse L, Reyes M, Faulkner J A, Chamberlain J S).

Wiskott-Aldrich-Syndrome is characterized by thrombocytopenia, dysregulation and propensity towards lymphoma development later in life and represents a potential target for engineered stem cell therapy (Dupre et al., 2006). Fanconi anemia, is considered a "stem cell disease" and has been the subject of intensive research for treatment using gene therapy. This disease represents the best-characterized congenital defect of hematopoietic stem cells. It is a rare hereditary disease characterized by bone marrow failure and developmental anomalies; a high incidence of myelodysplasia, acute nonlymphocytic leukemia, and solid tumors. The genetic basis for Fanconi anemia lies in selective mutations in any one of the known Fanconi anemia genes, making this disease a candidate for gene therapy. But the disease is complex as at least 12 genetic subtypes have been described (FA-A, -B, -C, -D1, -D2, -E, -F, -G, -I, -J, -L, -M) and all, with the exception of FA-I have been linked to a distinct gene. Most FA proteins form a complex that activates the FANCD2 protein via monoubiquitination, while FANCJ and FANCD1/BRCA2 function downstream of this step. The FA proteins typically lack functional domains, except for FANCJ/BRIP1 and FANCM, which are DNA helicases, and FANCL, which is probably an E3 ubiquitin conjugating enzyme. Based on the hypersensitivity to cross-linking agents, the FA proteins are thought to function in the repair of DNA interstrand cross-links, which block the progression of DNA replication forks. (*Cell Oncol.* 2006; 28 (1-2):3-29. The Fanconi anemia pathway of genomic maintenance. Levitus M, Joenie H, de Winter J P.

Additional inherited stem cell defects that are potential candidates for gene therapy include amegakaryocytic thrombocytopenia, dyskeratosis congenity and Shwachman-Diamond syndrome. Thalassemias and Sickle Cell disease belong to the group of hereditary hemolytic anemias that represent the most common inherited diseases worldwide and thus are important candidates for stem cell gene therapy (Persons and Tisdale, 2004).

A good example using genetically modified mesenchymal stem cells in a clinical setting is the correction of the genetic mutation in the bridled bone disease osteogenesis imperfecta. Osteogenesis imperfecta causes fragile bones due to mutations in the collagen-I-encoding genes, COLIA1 or COLIA2. Chamberlain et al. obtained mesenchymal stem cells (MSCs) from the bones of osteogenesis imperfecta patients and identified point mutations in the COLIA1 gene (Chamberlain et al., 2004). MSCs were successfully infected with an adeno-associated virus to target and deactivate the mutated COLIA1 gene. The corrected MSCs were then transplanted into immunodeficient mice and damaged cells demonstrated improved stability and collagen processing.

Examples

Example 1

Multipotent adult stem cells are isolated from the bone marrow and other sources of a patient or donor using adherent growth in-vitro to determine cell activity and biological function. At this in-vitro stage the adherent growing cell do not express the "stem cell marker" CD34 and are therefore considered CD34-negative during in-vitro culturing. At this stage, CD34-negative, adherent growing stem cells are transient or stably transfected by viral or non-viral technologies and expanded selectively in-vitro before in-vivo application. For the generation of transgenic CD34-negative progenitor cells two promoters are used for selection and organ/target-specific inducibility of the therapeutic gene. The gene transfer system is chosen based on their transfection and integration (if desired) combined with adhesion selectivity. As this example, the tie2-promotor enhancer is driving the HSV-TK gene, which is expressed only in the context of endothelial differentiation, which happens during tumor neo-angiogenesis. While circulating endogenous as well as systemically administered stem cells are recruited physiologically to the site of tumor growth to participate in the tumor neo-angiogenesis (independently whether it is the primary tumor site or metastasis), the stem cells differentiate into tumor endothelial cells. During this process of organ-specific differentiation, the stem cells express the HSV-TK gene driven by the angiogenesis-related tie2 activation. Now the prodrug ganciclovir can be given to the patient and is converted by the HSV-TK into the cytotoxic substance at the site of tumor angiogenesis. This approach has been successfully shown in pre-clinical models for breast cancer, metastatic colo-rectal cancer, pancreas carcinoma and glioblastoma. An application can be envisioned for any (malignant) neoplasia that relies on tumor neo-angiogenesis. This approach aims at the disruption of tumor angiogenesis.

Example 2

As in EXAMPLE 1, but instead of expressing HSV-TK, expressing clotting substances as cytotoxic proteins.

Example 3

Angiogenesis is also a pivotal biological process in tissue remodeling and wound healing. This does not only apply for lesions of the skin or mucosa but also for other tissues, like the lack of insulin-producing beta-cells in the pancreas, leading to Insulin-dependent Diabetes mellitus (IDDM). The systemic application of transgenic CD34-negative progenitor cells can also induce the activation of otherwise quiescent islet progenitor cells in the pancreas, replenishing the endocrine pancreas and correcting the state of hyperglycemia in IDDM patients. The tie-2 enhancer promoter activates the gene for vasoactive substances like VEGF promoting tissue remodeling and wound healing.

Example 4

As in EXAMPLE 3, but in combination with the transplantation of allogeneic islet cells if endogenous regeneration is not sufficient anymore.

Example 5

As in EXAMPLE 1, but transgenic cells with enhanced homing capabilities to the site of tumor growth, tissue remodeling or wound healing applying chemokine biology. CD34-negative, adherent growing stem cells are engineered using GPI-mucin-chemokines. These agents will allow the selective expression of specific chemokines linked to the mucin-domain taken either from CX3CL1 or CXC16 fused to a GPI anchor. The expression of these chemokine-mucin agents will recruit complementary leukocytes expressing the chemokine receptor. For example, CXCL10-mucin-GPI expression under the control of the tie2 promoter enhancer in the context of tumor therapy will facilitate the recruitment of effector T cells into the tumor environment. This will act as an adjuvant for tumor immune therapy. The same approach could also be used in tissue remodeling to facilitate the parallel recruitment of select leukocyte populations.

Example 6

As in EXAMPLE 1, but genetically engineering CD34-negative stem cells that can modulate the inflammatory environment, e.g. in autoimmune disorders like chronic-inflammatory bowel disease or graft-versus-host disease after allogeneic bone marrow/stem cell transplantation. This can also be facilitated by the site-specific expression of anti-inflammatory substances like interleukins (IL-10).

Example 7

As in EXAMPLE 1, but with the site-specific expression of common viral antigens e.g. which induce an internal vaccination boost at the site of tumor growth, e.g. measles or chicken pox.

Example 8

As in EXAMPLE 1, but the therapeutic gene activation is suppressed by genes of an early developmental stage (e.g. Noggin), which eventually becomes down regulated during the differentiation of the transgenic progenitor cells in mature tissue at the site of the tumor or tissue remodeling/regeneration.

Part II

Breast and Pancreatic Tumor Models

Synopsis

Tumor angiogenesis represents a promising target for the selective delivery of cancer therapeutics. Bone marrow—derived mesenchymal stem cells were developed to selectively target exogenous genes to tumor angiogenesis environments. The results of these experiments show that exogenously added MSC home to tumors where they undergo differentiation. Genes such as the RFP reporter gene as well as the suicide gene HSV-tk are selectively expressed during differentiation under control of the Tie2 promoter/enhancer. The administration of the pro-drug ganciclovir in concert with tk expression effectively targets the tumor and results in the suppression of tumor growth.

Endogenous Mouse Breast Cancer Model

A previously established murine breast cancer model was used by Dr. Christoph Klein to study the use of engineered MSC in tumor angiongenesis. This model is broadly applicable to human breast cancer. In this model, transgenic mice carrying the activated rat c-neu oncogene under transcriptional control of the MMTV promoter have been backcrossed to BALB/c mice with the aim of developing a broadly applicable model for cancer therapy. Female HER-2/neu (neu-N) transgenic mice, which express the nontransforming rat proto-oncogene, develop spontaneous focal mammary adeno-carcinomas beginning at 5-6 months of age. The development and histology of these tumors bear resemblance to what is seen in patients with breast cancer.

Expression of RFP and GFP Genes in imMSC Under Control of Endothelial Specific Promoters in the Context of Tumor Angiogenesis To assess the control of tissue specific expression gene expression in imMSC in the context of tumor angiogenesis, and to follow the distribution of imMSCs over longer time periods microscopically, red and green fluorescent protein (RFP, GFP) genes have been cloned into modified expression vectors to detect in vivo.

Mice

Female HER-2/neu (neu-N) transgenic mice expressing the nontransforming rat proto-oncogene, are known to develop spontaneous focal mammary adeno-carcinomas at 5-6 months of age. BALB-neuT transgenic mice were maintained in accordance with the Agreement to the European Union Guidelines. Mice were screened for hemizygosity (neuT+/neuT−). Mammary glands of Balb-neuT female mice were inspected twice a week and arising tumors were measured.

Figure 5:
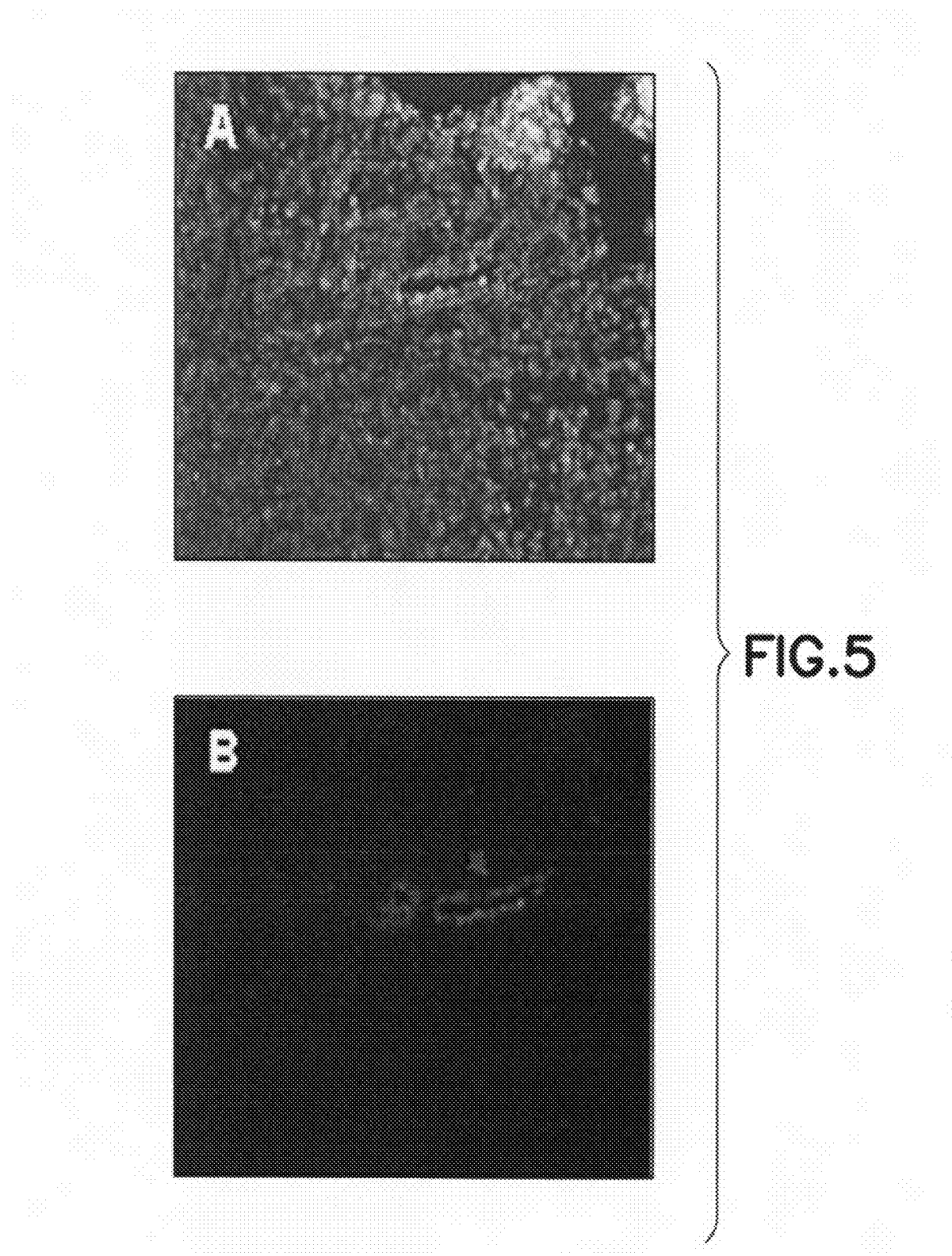
Figure 6:
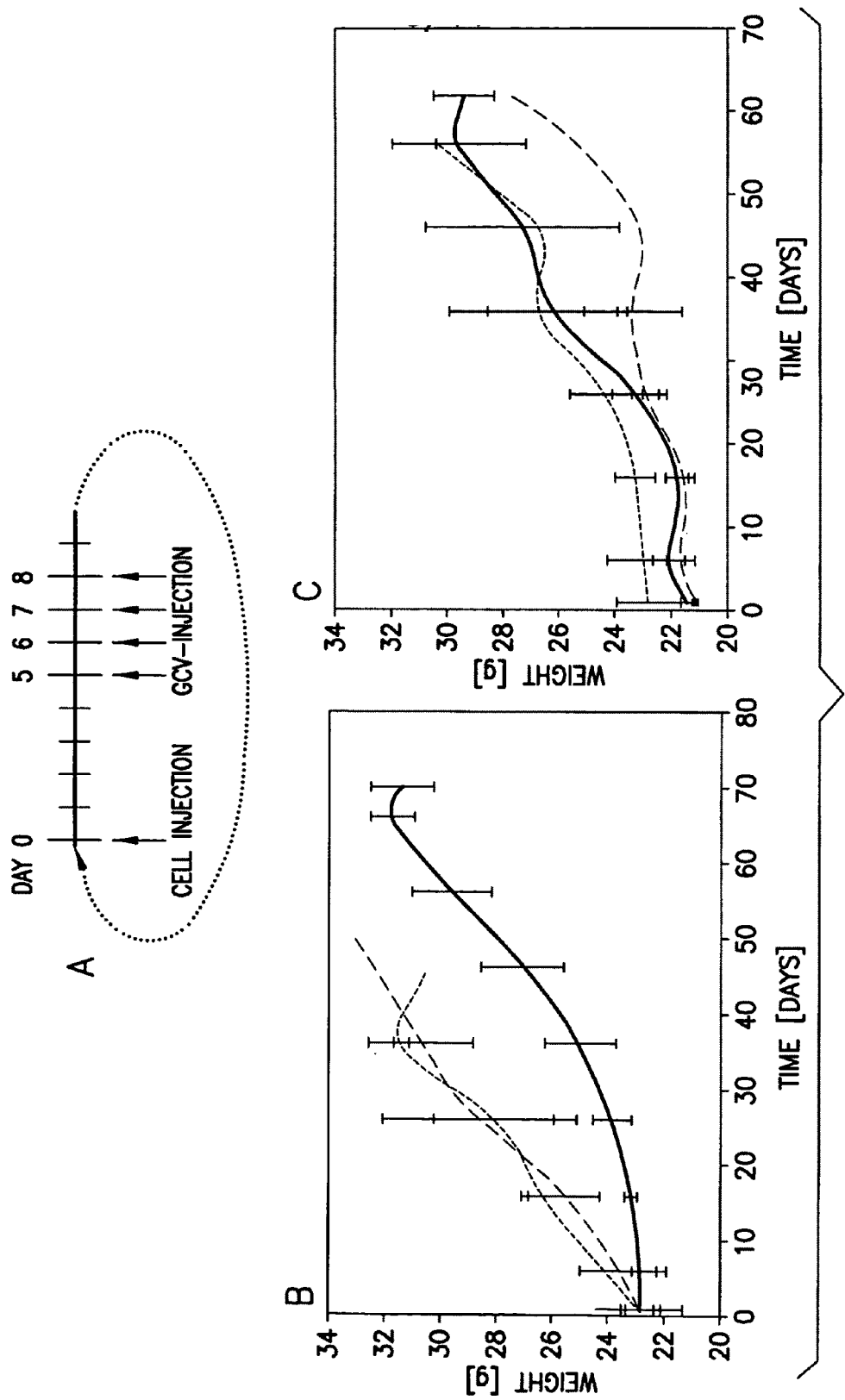
Figure 7:
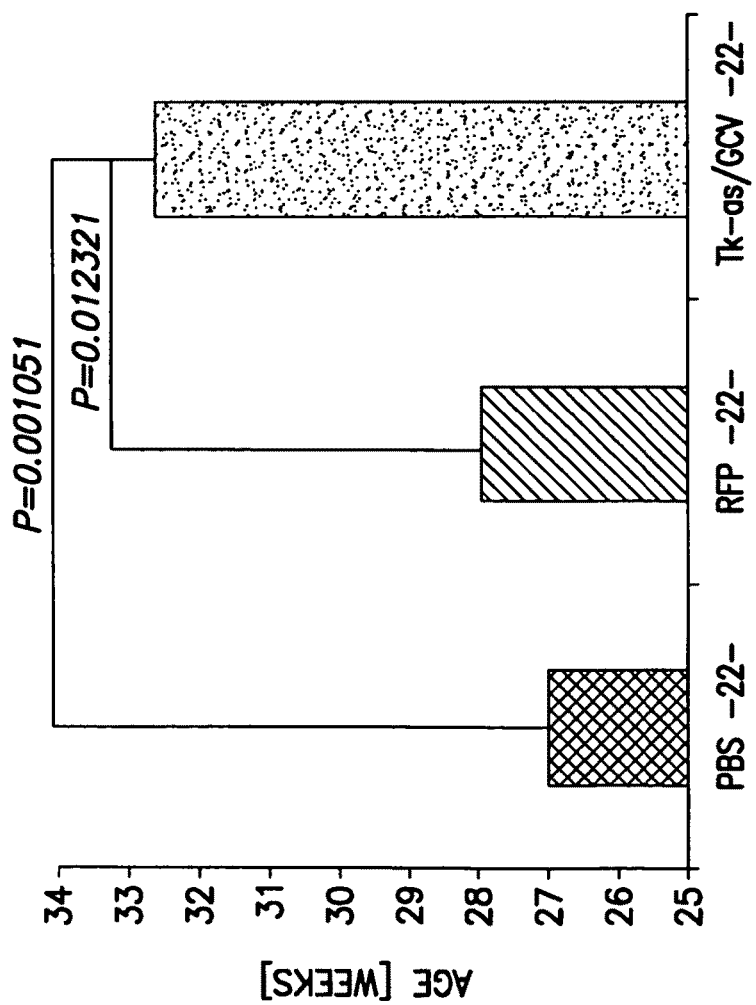

The genetically modified cells were injected into the breast cancer model mice following surgical resection of the primary tumor. As the residual tumor grew back, the exogenously added imMSC provided precursor cells for neovascularization. The Tie-2-RFP (endothelial specific promoter driving red florescence protein) stably transfected imMSCs were found to readily home to the tumor, differentiate to endothelial cells, and express the RFP reporter gene (FIG. 5). In these experiments the integration of the mesenchymal cells into the primary mammary tumors of Balb-neuT mice was evaluated. After three applications of RFP-transfected, RFP-expressing cells could be detected in vessel-like regions in all sections. The results demonstrate that the cells home to sites of neovascularization and express marker genes through the activated Tie2 promoter/enhancer.

Inhibiting Tumor Growth by Targeting a Suicide Gene in the Endothelium

The protocol was then altered to evaluate the effect of the suicide gene HSV-tk. The tk gene product in combination with the prodrug ganciclovir (GCV) produces a potent toxin which affects replicative cells. ImMSCs were stably transfected with plasmids carrying the herpes simplex virus-thymidine kinase (tk) gene driven by the vascular endothelial Tie2 promoter/enhancer. To this end, the murine model of breast cancer angiogenesis was used again to evaluate the engineered MSC line in anti-angiogenesis therapy. Approach I. Injection of engineered MSC and ganciclovir® treatment in the phase of exponential tumor growth at the age of 18 or 22 weeks Approach I. Injection of Engineered MSC and Ganciclovir® Treatment in the Phase of Exponential Tumor Growth at the Age of 18 or 22 Weeks The Treatment of Balb-neuT trsg Mice started on day 0 (week 22), with injection of 0.2 ml cells (500,000 cells) and 0.2 ml PBS as control. On days 5 to 8, ganciclovir was applied in a daily dose of 30 μg/g BW, e.g. 100 μl for a mouse with 21 g BW. After day 9, mice treatment cycles were repeated until dissection. During the treatment tumor progression, bodyweight (measured on day 0 and 6 of each therapy cycle) and behavior were recorded.

To get an overall impression of the effect of the treatment with Tie2-Tk-as-transfected cells and GCV respectively compared with both control groups, the macroscopic value of bodyweight was recorded during treatment until dissection. Measure points were days 0 and 5 of each cycle of therapy and the day of dissection. The experiments included one treatment and two control groups of mice and started at two different time points, 18 and 22 weeks of age.

TABLE 2

Data of treatment groups after dissection, including bodyweight, absolute and relative tumor load.

| Treatment group | Amount of mice | Bodyweight [g] | SD | Absolute tumourload [g] | SD | Relative tumourload [g] | SD |
|---|---|---|---|---|---|---|---|
| PBS - 22 - | 2 | 32.6 | 0.8 | 8.5 | 1 | 0.265 | 0.035 |
| RFP - 22 - | 3 | 29.4 | 3 | 8.3 | 0.9 | 0.287 | 0.032 |
| Tk-as/ GCV- 22 - | 3 | 31.8 | 1.1 | 8.1 | 0.9 | 0.257 | 0.021 |

Approach II. Evaluation of Therapy in the Context of Tumor Regrowth Following Surgical Resection In patients following the surgical removal of a tumor, residual tumor that is missed during surgery often grows out, leading to a reoccurrence of cancer. To test the efficacy of the engineered MSC/tk therapy in this context, the breast tissue from Balb/c neu-N transgenic mice was resected at 18 weeks of age, leading to a delayed onset of primary tumor. Following surgery, the mice were treated with the MSC-tk and GCV regimen as described above. The treatment resulted in a dramatic reduction in tumor growth in the treated mice (FIG. 8).

Pancreatic Tumor Model

Figure 9:
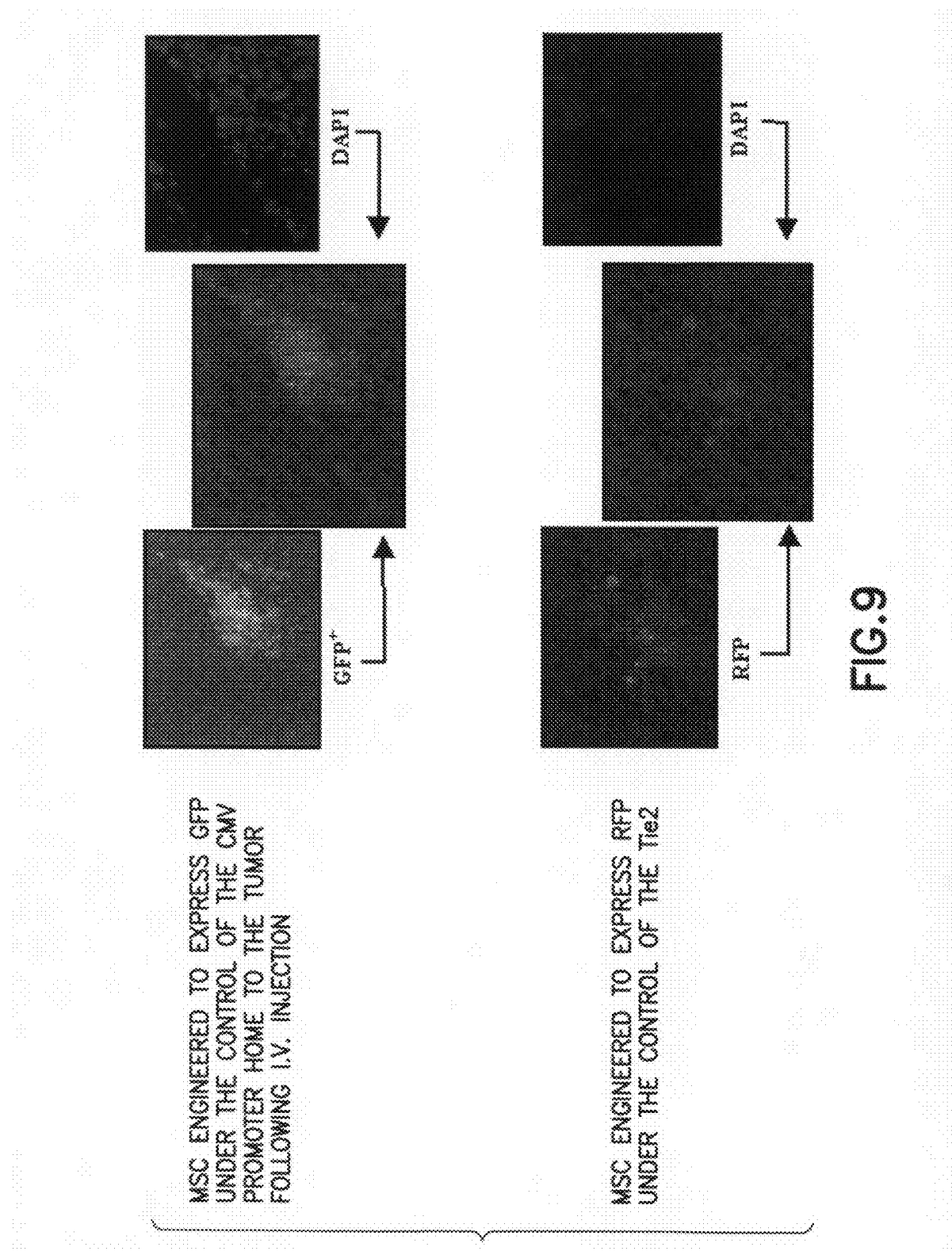
Figure 10:
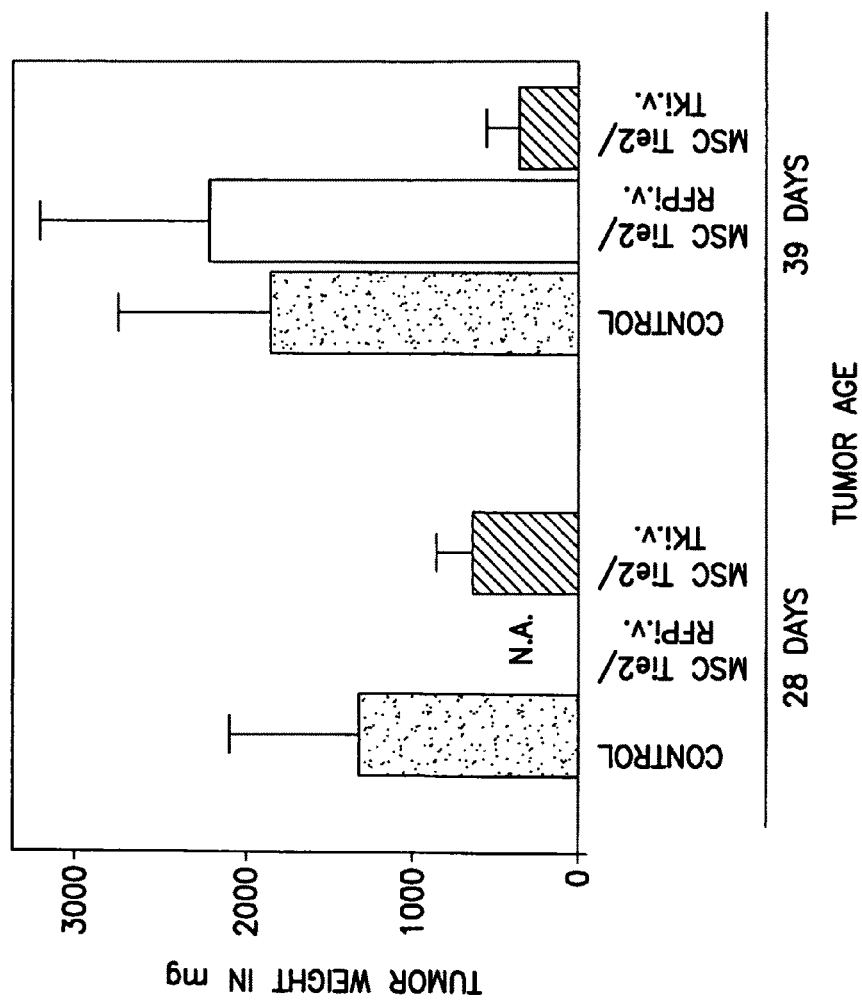
Figure 11:
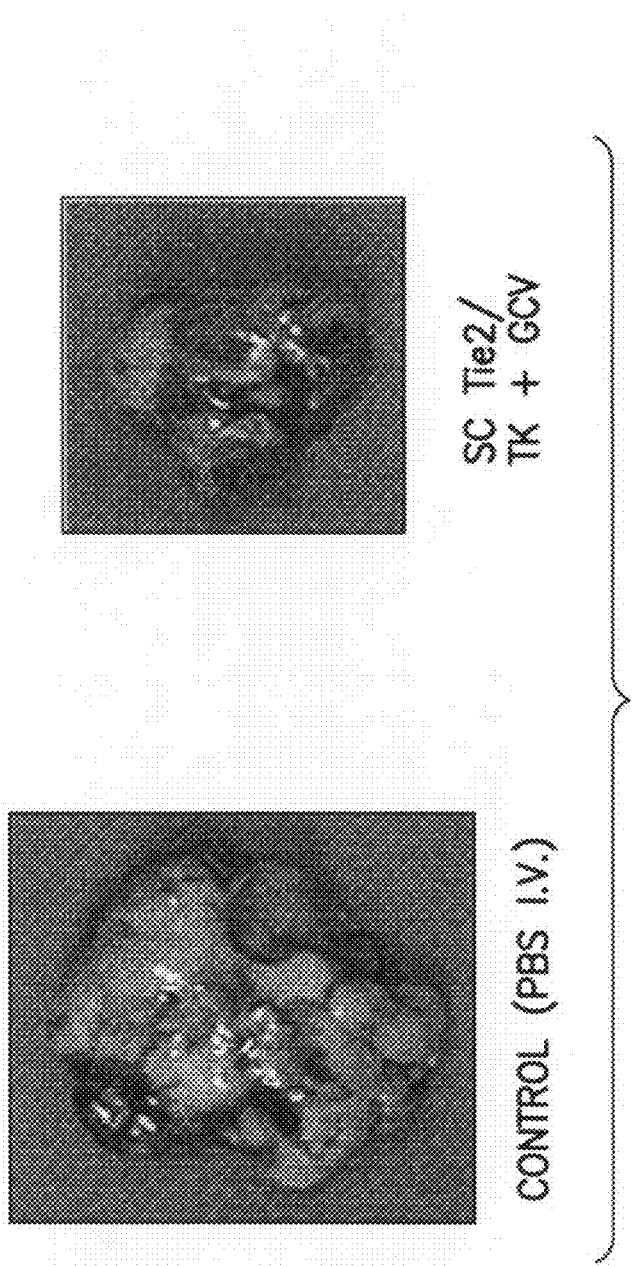

An orthotopic pancreatic carcinoma model was then developed in C57Bl/6 mice to assess the efficacy of the MSC-based therapy in a different tumor system. The system had been previously established by Christiane Bruns and Claudius Conrad (Surgery Department, LMU). In this model, Panc02 pancreatic carcinoma cells syngeneic to C57Bl/6 mice were injected subcapsularly in a region of the pancreas just beneath the spleen to create primary pancreatic tumors. Constructs with GFP under the control of the CMV promoter, and RFP and tk under the control of Tie2 promoter/enhancer, were introduced into the MSC isolated from C57Bl/6 mice. The transfected stem cells were given systemically via i.v. injections. In a preliminary experiment, MSC engineered to constitutively express GFP (under control of the CMV promoter) were injected into mice with growing tumors. The cells were found to efficiently home to the tumors (FIG. 9).

In parallel experiments, mice with growing tumors were injected with the Tie2-RFP engineered MSC. After five days, the animals were sacrificed and the tumors were examined for expression of RFP. The results show a strong upregulation of RFP in the context of tumor (FIG. 9). RFP was not detected in other organs (spleen, lymph nodes and thymus).

REFERENCES

Aiuti, A, Slavin, S, Aker, M, Ficara, F, Deola, S, Mortellaro, A, Morecki, S, Andolfi, G, Tabucchi, A, Carlucci, F, Marinello, E, Cattaneo, F, Vai, S, Servida, P, Miniero, R, Roncarolo, M G, Bordignon, C (2002) Correction of ADA-SCID by stem cell gene therapy combined with nonmyeloablative conditioning. Science 296: 2410-2413.

Aluigi, M G, Angelini, C, Falugi, C, Fossa, R, Genever, P, Gallus, L, Layer, P G, Prestipino, G, Rakonczay, Z, Sgro, M, Thielecke, H, Trombino, S (2005) Interaction between organophosphate compounds and cholinergic functions during development. Chem Biol Interact 157-158: 305-316.

Armentano, D, Sookdeo, C C, Hehir, K M, Gregory, R J, St George, J A, Prince, G A, Wadsworth, S C, Smith, A E (1995) Characterization of an adenovirus gene transfer vector containing an E4 deletion. Hum Gene Ther 6: 1343-1353.

Atchison, R W, Casto, B C, Hammon, W M (1965) Adenovirus-Associated Defective Virus Particles. Science 149: 754-756.

Atchison, R W, Casto, B C, Hammon, W M (1966) Electron microscopy of adenovirus-associated virus (AAV) in cell cultures. Virology 29: 353-357.

Baekelandt, V, De Strooper, B, Nuttin, B, Debyser, Z (2000) Gene therapeutic strategies for neurodegenerative diseases. Curr Opin Mol Ther 2: 540-554.

Barese, C N, Goebel, W S, Dinauer, M C (2004) Gene therapy for chronic granulomatous disease. Expert Opin Biol Ther 4: 1423-1434.

Becerra, S P, Koczot, F, Fabisch, P, Rose, J A (1988) Synthesis of adeno-associated virus structural proteins requires both alternative mRNA splicing and alternative initiations from a single transcript. J Virol 62: 2745-2754.

Bendas, G (2001) Immunoliposomes: a promising approach to targeting cancer therapy. BioDrugs 15: 215-224.

Benihoud, K, Yeh, P, Perricaudet, M (1999) Adenovirus vectors for gene delivery. Curr Opin Biotechnol 10: 440-447.

Bett, A J, Haddara, W, Prevec, L, Graham, F L (1994) An efficient and flexible system for construction of adenovirus vectors with insertions or deletions in early regions 1 and 3. Proc Natl Acad Sci USA 91: 8802-8806.

Beyer, W R, Westphal, M, Ostertag, W, von Laer, D (2002) Oncoretrovirus and lentivirus vectors pseudotyped with lymphocytic choriomeningitis virus glycoprotein: generation, concentration, and broad host range. J Virol 76: 1488-1495.

Bradfute, S B, Goodell, M A (2003) Adenoviral transduction of mouse hematopoietic stem cells. Mol Ther 7: 334-340.

Buning, H, Nicklin, S A, Perabo, L, Hallek, M, Baker, A H (2003) AAV-based gene transfer. Curr Opin Mol Ther 5: 367-375.

Cao, H, Koehler, D R, Hu, J (2004) Adenoviral vectors for gene replacement therapy. Viral Immunol 17: 327-333.

Cavazzana-Calvo, M, Hacein-Bey, S, de Saint Basile, G, Gross, F, Yvon, E, Nusbaum, P, Selz, F, Hue, C, Certain, S, Casanova, J L, Bousso, P, Deist, F L, Fischer, A (2000) Gene therapy of human severe combined immunodeficiency (SCID)-X1 disease. Science 288: 669-672.

Chamberlain, J R, Schwarze, U, Wang, P R, Hirata, R K, Hankenson, K D, Pace, J M, Underwood, R A, Song, K M, Sussman, M, Byers, P H, Russell, D W (2004) Gene targeting in stem cells from individuals with osteogenesis imperfecta. Science 303: 1198-1201.

Cochrane, A W, Chen, C H, Rosen, C A (1990) Specific interaction of the human immunodeficiency virus Rev protein with a structured region in the env mRNA. Proc Natl Acad Sci USA 87: 1198-1202.

Dancer, A, Julien, S, Bouillot, S, Pointu, H, Vernet, M, Huber, P (2003) Expression of thymidine kinase driven by an endothelial-specific promoter inhibits tumor growth of Lewis lung carcinoma cells in transgenic mice. Gene Ther 10: 1170-1178.

Danthinne, X, Imperiale, M J (2000) Production of first generation adenovirus vectors: a review. Gene Ther 7: 1707-1714.

Danthinne, X, Werth, E (2000) New tools for the generation of E1- and/or E3-substituted adenoviral vectors. Gene Ther 7: 80-87.

Derossi, D, Calvet, S, Trembleau, A, Brunissen, A, Chassaing, G, Prochiantz, A (1996) Cell internalization of the third helix of the Antennapedia homeodomain is receptor-independent. J Biol Chem 271: 18188-18193.

Dupre, L, Marangoni, F, Scaramuzza, S, Trifari, S, Hernandez, R J, Aiuti, A, Naldini, L, Roncarolo, M G (2006) Efficacy of gene therapy for Wiskott-Aldrich syndrome using a WAS promoter/cDNA-containing lentiviral vector and nonlethal irradiation. Hum Gene Ther 17: 303-313.

Dymecki, S M (1996) Flp recombinase promotes site-specific DNA recombination in embryonic stem cells and transgenic mice. Proc Natl Acad Sci USA 93: 6191-6196.

Emerman, M, Temin, H M (1986) Quantitative analysis of gene suppression in integrated retrovirus vectors. Mol Cell Biol 6: 792-800.

Felnerova, D, Viret, J F; Gluck, R, Moser, C (2004) Liposomes and virosomes as delivery systems for antigens, nucleic acids and drugs. Curr Opin Biotechnol 15: 518-529.

Fessele, S, Maier, H, Zischek, C, Nelson, P J, Werner, T (2002) Regulatory context is a crucial part of gene function. Trends Genet. 18: 60-63.

Flierl, A, Chen, Y, Coskun, P E, Samulski, R J, Wallace, D C (2005) Adeno-associated virus-mediated gene transfer of the heart/muscle adenine nucleotide translocator (ANT) in mouse. Gene Ther 12: 570-578.

Gabriel, B, Teissie, J (1997) Direct observation in the millisecond time range of fluorescent molecule asymmetrical interaction with the electropermeabilized cell membrane. Biophys J 73: 2630-2637.

Gaspar, H B, Parsley, K L, Howe, S, King, D, Gilmour, K C, Sinclair, J, Brouns, G, Schmidt, M, Von Kalle, C, Barington, T, Jakobsen, M A, Christensen, H O, A I Ghonaium, A, White, H N, Smith, J L, Levinsky, R J, Ali, R R, Kinnon, C, Thrasher, A J (2004) Gene therapy of X-linked severe combined immunodeficiency by use of a pseudotyped gammaretroviral vector. Lancet 364: 2181-2187.

Ginsburg, D S, Calos, M P (2005) Site-specific integration with phiC31 integrase for prolonged expression of therapeutic genes. Adv Genet. 54: 179-187.

Giordano, F A, Fehse, B, Hotz-Wagenblatt, A, Jonnakuty, S, del Val, C, Appelt, J U, Nagy, K Z, Kuehicke, K, Naundorf, S, Zander, A R, Zeller, W J, Ho, A D, Fruehauf, S, Laufs, S (2006) Retroviral vector insertions in T-lymphocytes used for suicide gene therapy occur in gene groups with specific molecular functions. Bone Marrow Transplant 38: 229-235.

Grill, R J, Blesch, A, Tuszynski, M H (1997) Robust growth of chronically injured spinal cord axons induced by grafts of genetically modified NGF-secreting cells. Exp Neurol 148: 444-452.

Hagan, M, Wennersten, A, Meijer, X, Holmin, S, Wahlberg, L, Mathiesen, T (2003) Neuroprotection by human neural progenitor cells after experimental contusion in rats. Neurosci Lett 351: 149-152.

Hammerling, G J, Ganss, R (2006) Vascular integration of endothelial progenitors during multistep tumor progression. Cell Cycle 5: 509-511.

Heegaard, E D, Brown, K E (2002) Human parvovirus B19. Clin Microbiol Rev 15: 485-505.

Heng, B C, Haider, H K, Sim, E K, Cao, T, Tong, G Q, Ng, S C (2005) Comments about possible use of human embryonic stem cell-derived cardiomyocytes to direct autologous adult stem cells into the cardiomyogenic lineage. Acta Cardiol 60: 7-12.

Herzog, R W, Cao, O, Hagstrom, J N, Wang, L (2006) Gene therapy for treatment of inherited haematological disorders. Expert Opin Biol Ther 6: 509-522.

Huss, R, von Luttichau, I, Lechner, S, Notohamiprodjo, M, Seliger, C, Nelson, P (2004) [Chemokine directed homing of transplanted adult stem cells in wound healing and tissue regeneration]. Verh Dtsch Ges Pathol 88: 170-173.

Izsvak, Z, Ivics, Z, Plasterk, R H (2000) Sleeping Beauty, a wide host-range transposon vector for genetic transformation in vertebrates. J Mol Biol 302: 93-102.

Jackson, R J (2005) Alternative mechanisms of initiating translation of mammalian mRNAs. Biochem Soc Trans 33: 1231-1241.

Jin, H, Aiyer, A, Su, J, Borgstrom, P, Stupack, D, Friedlander, M, Varner, J (2006) A homing mechanism for bone marrow-derived progenitor cell recruitment to the neovasculature. J Clin Invest 116: 652-662.

Joliot, A, Prochiantz, A (2004) Transduction peptides: from technology to physiology. Nat Cell Biol 6: 189-196.

Kaminski, J M, Huber, M R, Summers, J B, Ward, M B (2002) Design of a nonviral vector for site-selective, efficient integration into the human genome. Faseb J 16: 1242-1247.

Kanerva, A, Hemminki, A (2005) Adenoviruses for treatment of cancer. Ann Med 37: 33-43.

Kochanek, S, Schiedner, G, Volpers, C (2001) High-capacity 'gutless' adenoviral vectors. Curr Opin Mol Ther 3: 454-463.

Kojaoghlanian, T, Flomenberg, P, Horwitz, M S (2003) The impact of adenovirus infection on the immunocompromised host. Rev Med Virol 13:155-171.

Kosaka, Y, Kobayashi, N, Fukazawa, T, Totsugawa, T, Maruyama, M, Yong, C, Arata, T, Ikeda, H, Kobayashi, K, Ueda, T, Kurabayashi, Y, Tanaka, N (2004) Lentivirus-based gene delivery in mouse embryonic stem cells. Artif Organs 28: 271-277.

Lakso, M, Sauer, B, Mosinger, B, Jr., Lee, E J, Manning, R W, Yu, S H, Mulder, K L, Westphal, H (1992) Targeted oncogene activation by site-specific recombination in transgenic mice. Proc Natl Acad Sci USA 89: 6232-6236.

Neff, T, Beard, B C, Kiem, H P (2006) Survival of the fittest: in vivo selection and stem cell gene therapy. Blood 107: 1751-1760.

Neff, T, Blau, C A (2001) Pharmacologically regulated cell therapy. Blood 97: 2535-2540.

O'Connor, T P, Crystal, R G (2006) Genetic medicines: treatment strategies for hereditary disorders. Nat Rev Genet. 7: 261-276.

Orban, P C, Chui, D, Marth, J D (1992) Tissue- and site-specific DNA recombination in transgenic mice. Proc Natl Acad Sci USA 89: 6861-6865.

Pasanen, T, Hakkarainen, T, Timonen, P, Parkkinen, J, Tenhunen, A, Loimas, S, Wahlfors, J (2003) TK-GFP fusion gene virus vectors as tools for studying the features of HSV-TK/ganciclovir cancer gene therapy in vivo. Int J Mol Med 12: 525-531.

Persons, D A, Tisdale, J F (2004) Gene therapy for the hemoglobin disorders. Semin Hematol 41: 279-286.

Reyes, M, Dudek, A, Jahagirdar, B, Koodie, L, Marker, P H, Verfallie, C M (2002) Origin of endothelial progenitors in human postnatal bone marrow. J Clin Invest 109: 337-346.

Rodriguez, C I, Buchholz, F, Galloway, J, Sequerra, R, Kasper, J, Ayala, R, Stewart, A F, Dymecki, S M (2000)

High-efficiency deleter mice show that FLPe is an alternative to Cre-loxP. Nat Genet. 25: 139-140.

Rols, M P, Teissie, J (1990) Electropermeabilization of mammalian cells. Quantitative analysis of the phenomenon. Biophys J 58: 1089-1098.

Shindo, T, Matsumoto, Y, Wang, Q, Kawai, N, Tamiya, T, Nagao, S (2006) Differences in the neuronal stem cells survival, neuronal differentiation and neurological improvement after transplantation of neural stem cells between mild and severe experimental traumatic brain injury. J Med Invest 53: 42-51.

Smith-Arica, J R, Thomson, A J, Ansell, R, Chiorini, J, Davidson, B, McWhir, J (2003) Infection efficiency of human and mouse embryonic stem cells using adenoviral and adeno-associated viral vectors. Cloning Stem Cells 5: 51-62.

Sodroski, J, Wyatt, R, Olshevsky, U, Olshevsky, V, Moore, J (1996) Conformation of the HIV-1 gp 120 envelope glycoprotein. Antibiot Chemother 48: 184-187.

Suhr, S T, Gage, F H (1993) Gene therapy for neurologic disease. Arch Neurol 50: 1252-1268.

Tirona, R G, Kim, R B (2005) Nuclear receptors and drug disposition gene regulation. J Pharm Sci 94: 1169-1186.

Torchilin, V P (2006) Recent approaches to intracellular delivery of drugs and DNA and organelle targeting. Annu Rev Biomed Eng 8: 343-375.

Tranchant, I, Thompson, B, Nicolazzi, C, Mignet, N, Scherman, D (2004) Physicochemical optimisation of plasmid delivery by cationic lipids. J Gene Med 6 Suppl 1: S24-35.

Trobridge, G, Vassilopoulos, G, Josephson, N, Russell, D W (2002) Gene transfer with foamy virus vectors. Methods Enzymol 346: 628-648.

von Luettichau, I, Notohamiprodjo, M, Wechselberger, A, Peters, C, Henger, A, Seliger, C, Djafarzadeh, R, Huss, R, Nelson, P J (2005) Human Adult CD34− Progenitor Cells Functionally Express the Chemokine Receptors CCR1, CCR4, CCR7, CXCR5 and CCR10 but not CXCR4. Stem Cells Dev, Stem Cells Dev 14:329-336, 2005.

Wennersten, A, Meier, X, Holmin, S, Wahlberg, L, Mathiesen, T (2004) Proliferation, migration, and differentiation of human neural stem/progenitor cells after transplantation into a rat model of traumatic brain injury. J Neurosurg 100: 88-96.

Werner, T, Fessele, S, Maier, H, Nelson, P J (2003) Computer modeling of promoter organization as a tool to study transcriptional coregulation. Faseb J 17: 1228-1237.

Wu, N, Ataai, M M (2000) Production of viral vectors for gene therapy applications. Curr Opin Biotechnol 11: 205-208.

Young, L S, Searle, P F, Onion, D, Mautner, V (2006) Viral gene therapy strategies: from basic science to clinical application. J Pathol 208: 299-318.

Young, S M, Jr., Samulski, R J (2001) Adeno-associated virus (AAV) site-specific recombination does not require a Rep-dependent origin of replication within the AAV terminal repeat. Proc Natl Acad Sci USA 98: 13525-13530.

Young, S M, Jr., Xiao, W, Samulski, R J (2000) Site-specific targeting of DNA plasmids to chromosome 19 using AAV cis and trans sequences. Methods Mol Biol 133: 111-126.

Yu, J H, Schaffer, D V (2005) Advanced targeting strategies for murine retroviral and adeno-associated viral vectors. Adv Biochem Eng Biotechnol 99: 147-167.

Zernecke, A, Erl, W, Fraemohs, L, Lietz, M, Weber, C (2003) Suppression of endothelial adhesion molecule up-regulation with cyclopentenone prostaglandins is dissociated from IkappaB-alpha kinase inhibition and cell death induction. Faseb J 17: 1099-1101.

Deeg H J, Klingemann H G, Philips G L, A Guide to Bone Marrow Transplantation. Springer-Verlag Berlin Heidelberg 1992.

Remington: The Science and Practice of Pharmacy, 20th Ed., p. 808, Lippincott Williams & Wilkins (2000).

Yazawa K, Fisher W E, Brunicardi F C: Current progress in suicide gene therapy for cancer. World J Surg. 2002 July; 26 (7):783-9.

Schlaeger T M, Bartunkova S, Lawitts J A, Teichmann G, Risau W, Deutsch U, Sato T N. Uniform vascular-endothelial-cell-specific gene expression in both embryonic and adult transgenic mice. Proc Natl Acad Sci USA; 1997 94:3058-63.

J. Cell Physiol. 2007, Apr. 25 [Epub ahead of print].

We claim:

1. A method for treating a subject afflicted with a tumor comprising introducing into the subject's bloodstream a therapeutically effective number of genetically modified CD34− stem cells, wherein (a) each of the genetically modified CD34− stem cells contains an exogenous nucleic acid comprising (i) a cytotoxic protein-encoding region operably linked to (ii) a promoter or promoter/enhancer combination, whereby the cytotoxic protein is selectively expressed when the genetically modified CD34− stem cells come into proximity with, and differentiate into endothelial-like cells in proximity with, tumor tissue undergoing angiogenesis, directly and/or indirectly causing tumor tissue death, and (b) the introduction of the genetically modified CD34− stem cells is not preceded, accompanied or followed by myeloablation.

2. The method of claim 1, wherein the subject is human.

3. The method of claim 2, wherein the tumor is selected from the group consisting of a prostate tumor, a pancreatic tumor, a squamous cell carcinoma, a breast tumor, a melanoma, a basal cell carcinoma, a hepatocellular carcinoma, testicular cancer, a neuroblastoma, a glioma or a malignant astrocytic tumor such as glioblastma multiforme, a colorectal tumor, an endometrial carcinoma, a lung carcinoma, an ovarian tumor, a cervical tumor, an osteosarcoma, a rhabdo/leiomyosarcoma, a synovial sarcoma, an angiosarcoma, an Ewing sarcoma/PNET and a malignant lymphoma.

4. The method of claim 2, wherein the promoter/enhancer combination is the Tie2 promoter/enhancer, the cytotoxic protein is Herpes simplex viral thymidine kinase, and the subject is treated with ganciclovir in a manner permitting the Herpes simplex viral thymidine kinase to render the ganciclovir cytotoxic.

5. The method of claim 2, wherein the genetically modified CD34− stem cells are allogenic with respect to the subject.

6. The method of claim 2, wherein the genetically modified CD34− stem cells are autologous with respect to the subject.

7. The method of claim 2, wherein the therapeutically effective number of genetically modified CD34− stem cells is from about $1 \times 10^3$ to about $1 \times 10^7$ cells/kg body weight.

* * * * *